United States Patent
Jang et al.

(10) Patent No.: US 10,406,187 B2
(45) Date of Patent: Sep. 10, 2019

(54) **METHOD FOR TREATING NEUROINFLAMMATION WITH A PHARMACEUTICAL COMPOSITION CONTAINING *PORTULACA GRANDIFLORA* HOOK. EXTRACT OR FRACTION THEREOF AS ACTIVE INGREDIENT**

(71) Applicants: RESEARCH BUSINESS FOUNDATION SUNGKYUNKWAN UNIVERSITY, Suwon-si, Gyeonggi-do (KR); KOREA RESEARCH INSTITUTE OF BIOSCIENCE AND BIOTECHNOLOGY, Daejeon (KR)

(72) Inventors: Choon Gon Jang, Suwon-si (KR); Seung Hwan Kwon, Seoul (KR); Sang Ho Choi, Daejeon (KR); Wan Yi Li, Kunming (CN); Sang-Woo Lee, Daejeon (KR); Sei-Ryang Oh, Daejeon (KR); Hang Jin, Kunming (CN); Hyung Won Ryu, Daejeon (KR)

(73) Assignees: Research Business Foundation Sungkyunkwan University, Suwon-si (KR); Korea Research Institute of Bioscience and Biotechnology, Daejeon (KR)

(*) Notice: Subject to any disclaimer, the term of this patent is extended or adjusted under 35 U.S.C. 154(b) by 104 days.

(21) Appl. No.: 15/507,244

(22) PCT Filed: Aug. 27, 2015

(86) PCT No.: PCT/KR2015/008977
§ 371 (c)(1),
(2) Date: Sep. 11, 2017

(87) PCT Pub. No.: WO2016/032250
PCT Pub. Date: Mar. 3, 2016

(65) Prior Publication Data
US 2018/0125903 A1    May 10, 2018

(30) Foreign Application Priority Data
Aug. 27, 2014 (KR) .......... 10-2014-0112668

(51) Int. Cl.
A61K 36/185 (2006.01)
A61P 25/28 (2006.01)
A61P 25/16 (2006.01)

(52) U.S. Cl.
CPC ............ *A61K 36/185* (2013.01); *A61P 25/16* (2018.01); *A61P 25/28* (2018.01); *A61K 2236/33* (2013.01)

(58) Field of Classification Search
None
See application file for complete search history.

(56) References Cited

U.S. PATENT DOCUMENTS

2003/0036565 A1* 2/2003 Parkin .................... A61K 31/12
   514/683
2018/0251801 A1* 9/2018 Aharoni ................... A23L 5/46

FOREIGN PATENT DOCUMENTS

| CN | 1742866 A | 3/2006 |
| CN | 103948596 A | 7/2014 |
| KR | 10-2007-0065951 A | 6/2007 |
| KR | 10-2012 0117128 | * 10/2012 |
| KR | 10-2012-0117128 A | 10/2012 |
| KR | 10-2013-0011357 A | 1/2013 |

OTHER PUBLICATIONS

Rani N. et al. Cell Suspension Cultures of Portulaca grandiflora as Potent Catalysts . . . Pharmaceutical Biology 45(1)48-53, Jan. 2007. (Year: 2007).*
Liu et al., "Antimutagenicity screening of water extracts from 102 kinds of Chinese medicinal herbs", 1990, 640, pp. 617-622.
Nelson, PT. et al., "Microglia in diseases of the central nervous system" Annals of Medicine, 2002, 34, pp. 491-500.
Hui-Ming Gao et al., "Microglial activation—mediated delayed and progressive degeneration of rat nigral dopaminergic neurons: relevance to Parkinson's disease", Journal of Neurochemistry, 2002, 81, pp. 1285-1297.
W Sue T Griffin et al., "Interleukin-1 mediates Alzheimer and Lewy body pathologies" Journal of Neuroinflammation Mar. 5, 2006.
Manisha Gautam et al., "Therapeutic role of L-DOPA produced as a secondary metabolite from different legumes and plant sources" Annals of Phytomedicine, 2012, vol. 1, No. 2, 1-8.
Anghel, A. I. et al.: "Preliminary research on Portulaca grandiflora Hook. species (*Portulacaceae*) for therapeutic use", Farmacia, vol. 61, No. 4, 2013, pp. 694-702.
Chan, K. et al.: "The analgesic and anti-inflammatory effects of *Portulaca oleracea* L. subsp. *sativa* (Haw.) Celak", Journal of Ethnopharmacology, vol. 73, No. 3, 2000, pp. 445-451.
Rani Nisha et al: "Cell suspension cultures of Portulacagrandiflora as potent catalysts for biotransformation of L-tyrosine into L-OOPA, an antiParkinson's drug", Pharmaceutical Biology, vol. 45, No. 1, Dec. 31, 2006, pp. 48-53.

(Continued)

*Primary Examiner* — Ralph J Gitomer
(74) *Attorney, Agent, or Firm* — NSIP Law

(57) ABSTRACT

The present invention relates to a pharmaceutical composition and a food composition containing *Portulaca grandiflora* Hook. extract or a fraction thereof as an active ingredient for preventing, treating or ameliorating neuroinflammation or neuro-degenerative diseases. The *Portulaca grandiflora* Hook. extract or a fraction thereof according to the present invention is derived from a natural product which has been in use as a natural medicinal ingredient, and as such, has no side effects and inhibits expression of NO, $PGE_2$, iNOS and/or COX-2 genes or protein, which are factors associated with inflammation, and is additionally superbly effective for increasing and improving memory and the ability to learn, and thus can be beneficially used to prevent or treat neuroinflammation or neuro-degenerative diseases.

4 Claims, 28 Drawing Sheets

Specification includes a Sequence Listing.

(56) References Cited

OTHER PUBLICATIONS

Hongxing et al: "Neuroprotective effects of purslane herb aquenous extracts against d-galactose induced neurotoxicity", Chemico-Biological Interactions, vol. 170, No. 3, Nov. 15, 2007, pp. 145-152.
Zakaria M N M et al: "Evaluation of anti-inflammatory activity of *Portulaca* species", Journal of Pharmacy ano Pharmacology, vol. 50, Aug. 31, 1998, p. 227.

* cited by examiner

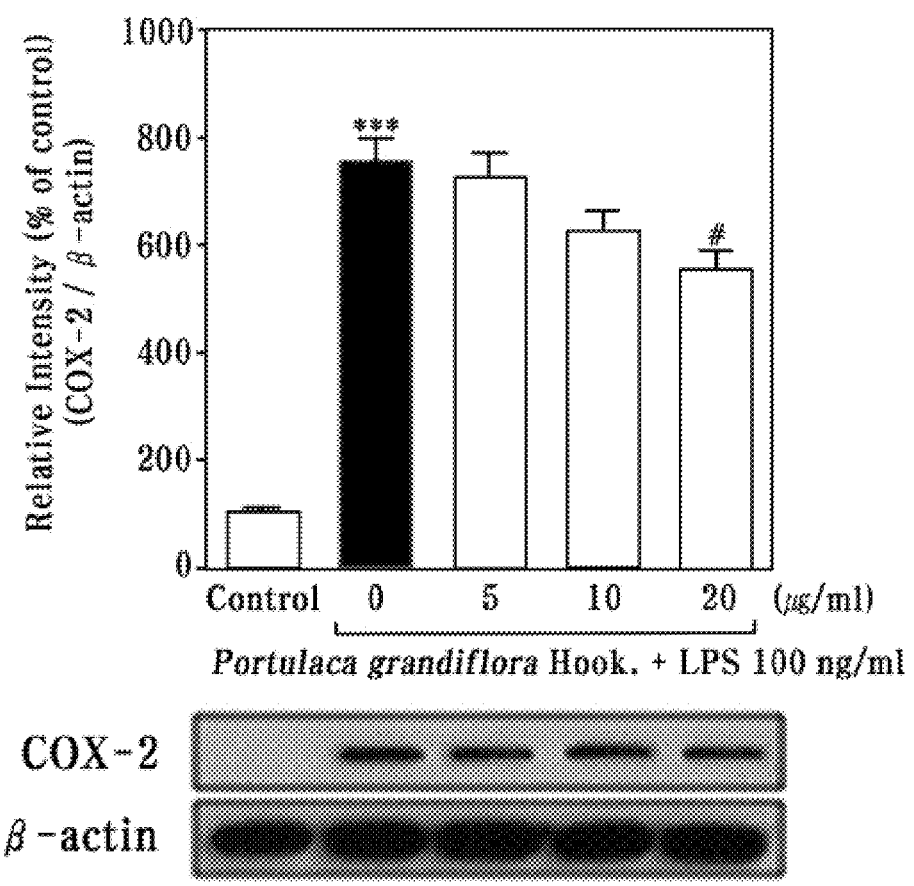

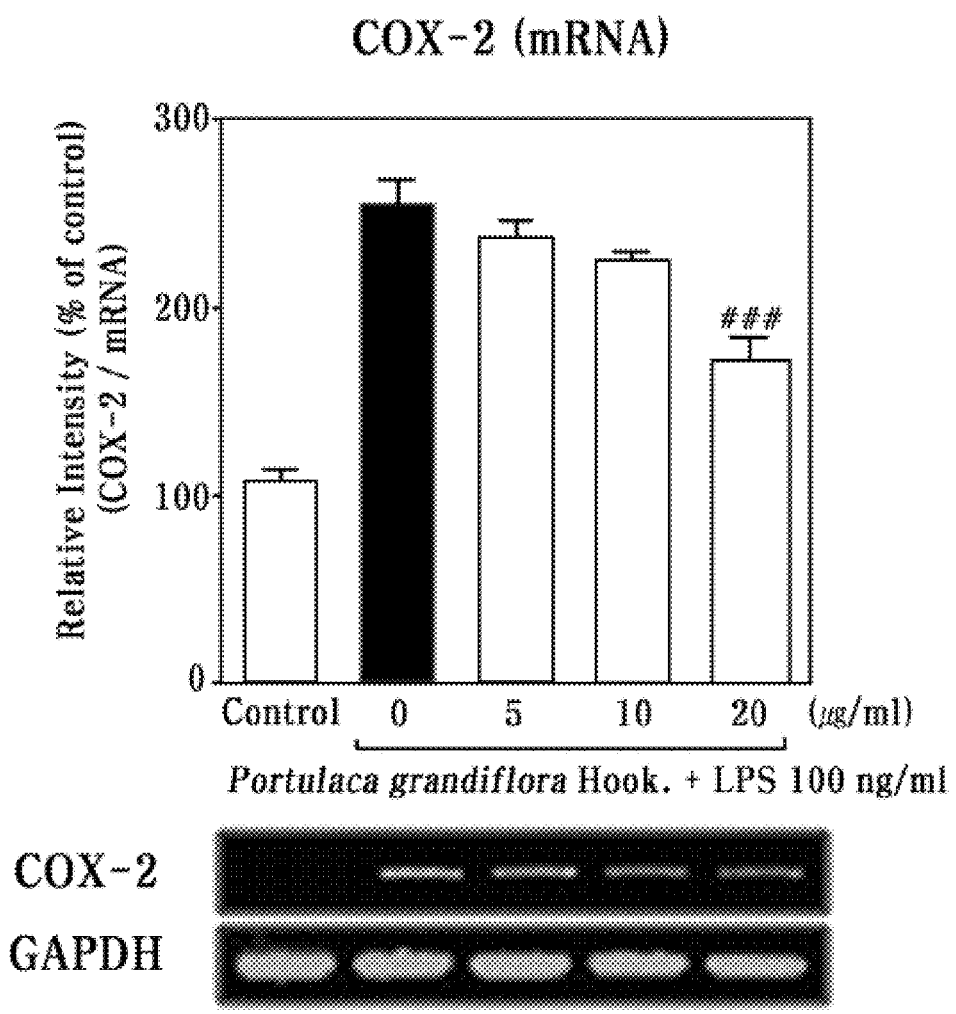

FIG. 6
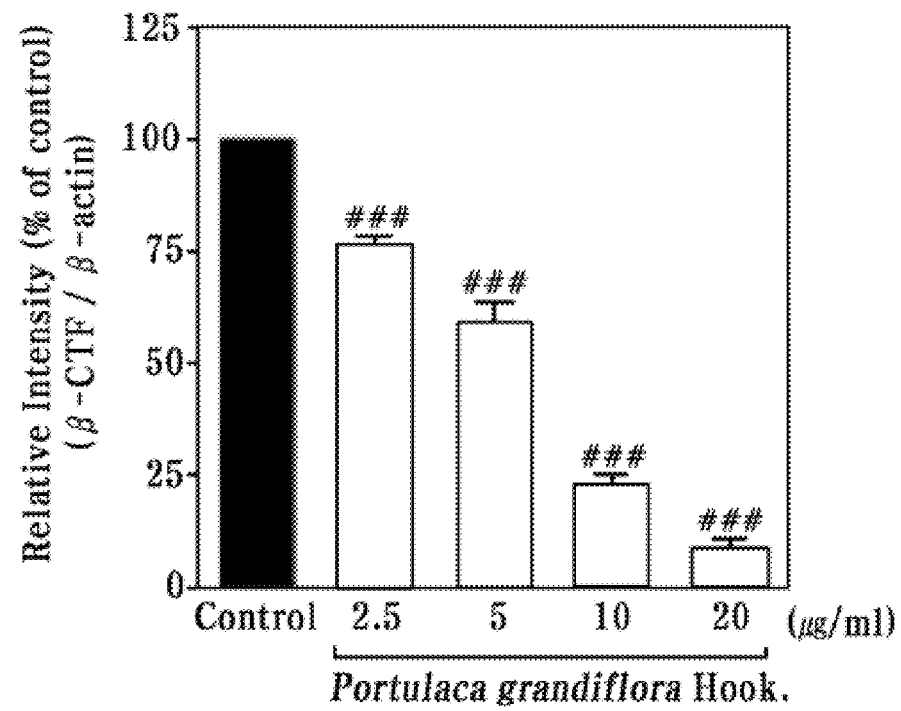
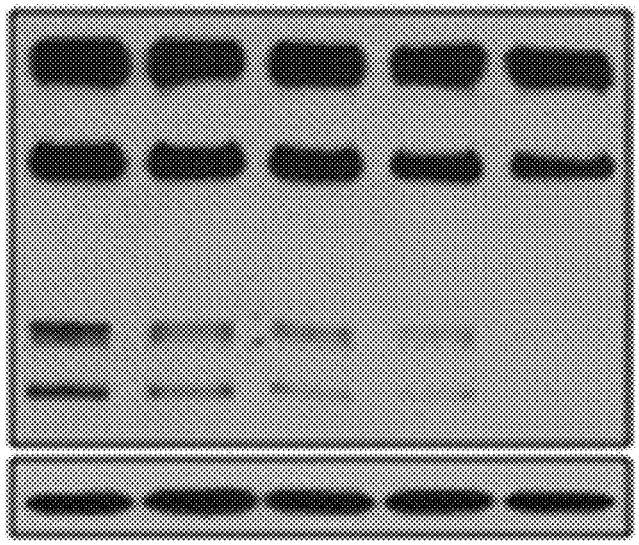

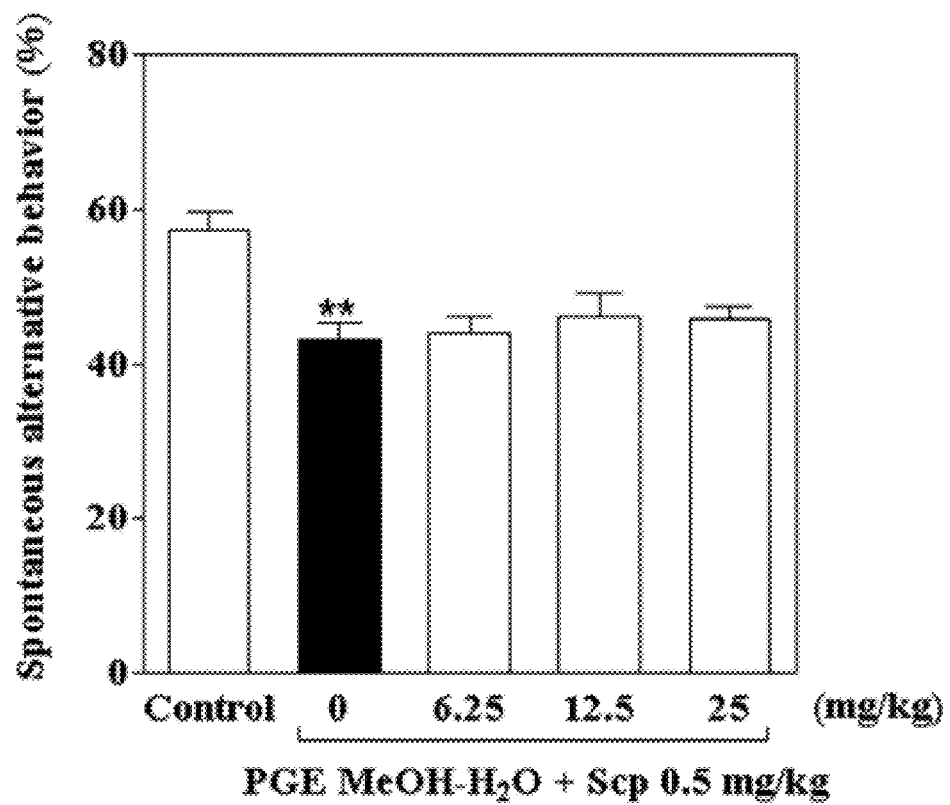

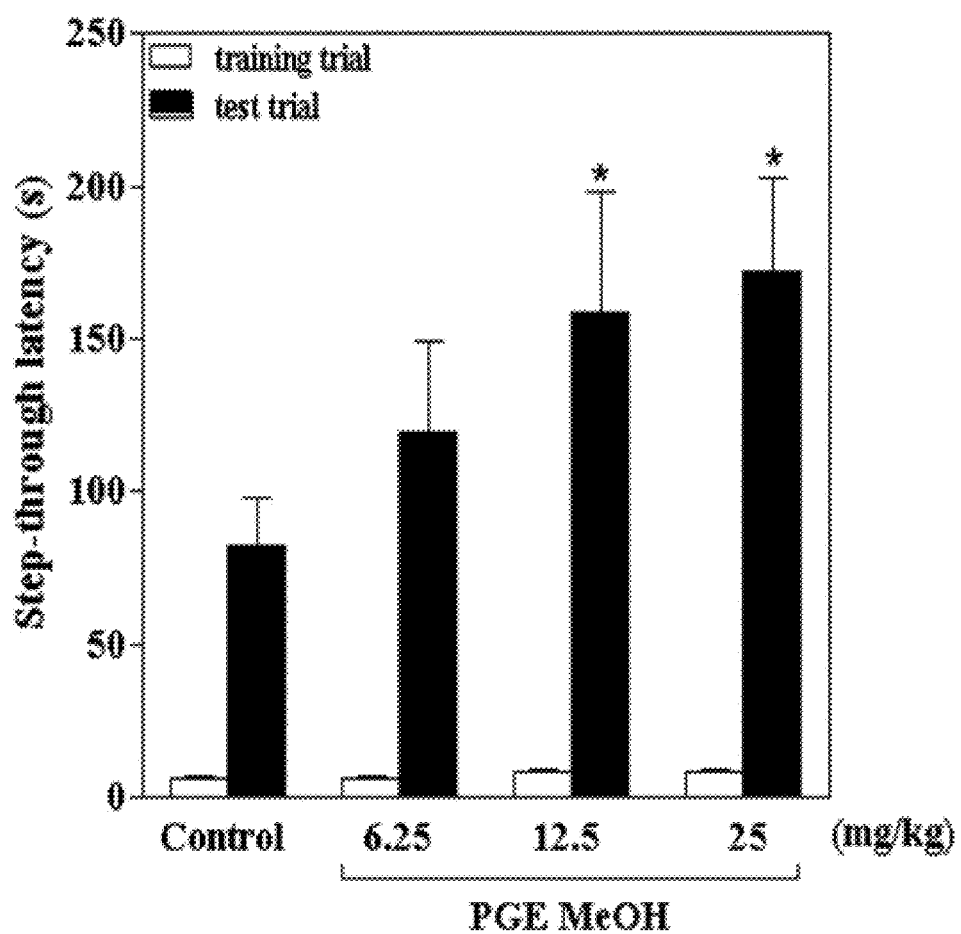

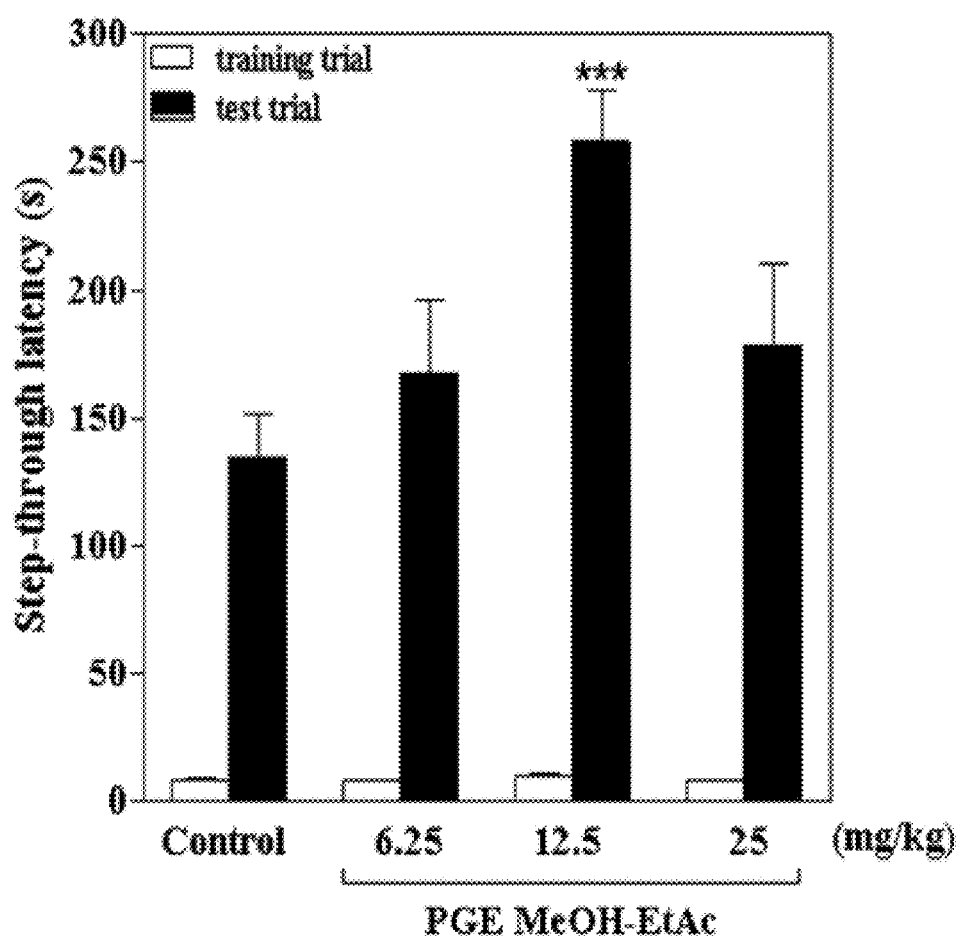

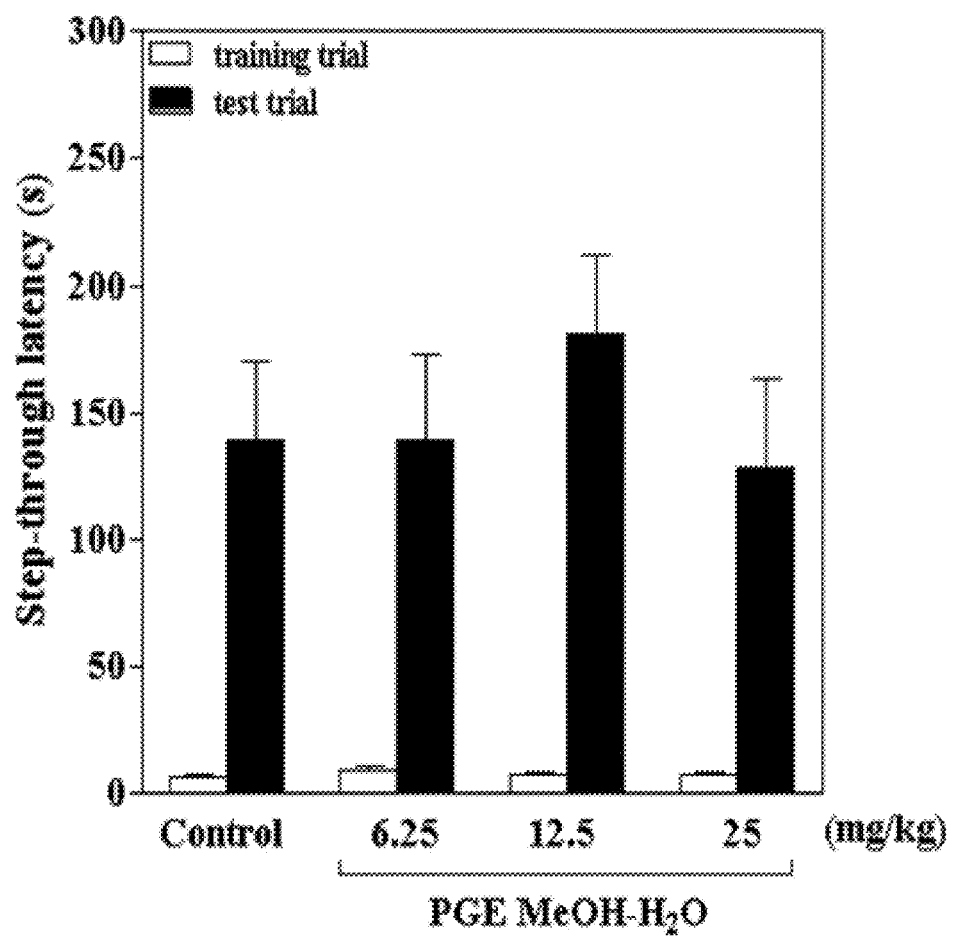

METHOD FOR TREATING NEUROINFLAMMATION WITH A PHARMACEUTICAL COMPOSITION CONTAINING *PORTULACA GRANDIFLORA* HOOK. EXTRACT OR FRACTION THEREOF AS ACTIVE INGREDIENT

CROSS-REFERENCE TO RELATED APPLICATIONS

This application is a 371 of PCT/KR2015/008977, filed Aug. 27, 2015, which claims the benefit of priority from Korean Patent Application No. 10-2014-0112668, filed Aug. 27, 2014, the contents of each of which are incorporated herein by reference.

TECHNICAL FIELD

The present invention relates to a pharmaceutical composition and a food composition containing a *Portulaca grandiflora* Hook. extract or a fraction thereof as an active ingredient for preventing, treating or ameliorating neuroinflammation or neuro-degenerative diseases.

BACKGROUND ART

When tissues (cells) are damaged or infected with invaders (bacteria, fungi, viruses, various types of allergens, etc.), the inflammatory response is associated with various inflammatory mediators and immunocytes in local blood vessels and bodily fluids to exhibit a series of complex physiological responses such as activation of enzymes, secretion of inflammatory mediators, infiltration of bodily fluids, cell migration, tissue destruction, etc., and external symptoms such as erythema, edema, fever, pain, etc. In normal cases, the inflammatory response serves to restore the function of organisms by removing the invaders and regenerating damaged tissues, but if antigens are not removed, or if the inflammatory response is excessive or persistent due to internal substances, it rather promotes damage of mucous membranes, and thus partially develops diseases such as cancer, etc.

In recent years, it has been found that the inflammatory response is one of major mechanisms of causing neurodegeneration. That is, microglial cells that are immunocytes present in the central nervous system may be activated by various exogenous and endogenous substances, and the activated microglial cells produce and release substances such as inflammatory cytokines TNF-α and IL-1β, nitrogen monoxide, prostaglandin, superoxide, etc. (Gao et al., *J Neurochem*, 81, 1285-97, 2002; Nelson, P T. et al., Ann Med, 34, 491-500, 2002; Griffin, W. S. et al., J Neuroinflammation, 3, 5, 2006). The production of such substances provokes immune responses in the short run, but the excessive or continuous production of the substances induces the death of neighboring nerve cells to cause neurodegeneration. Also, since substances released by dying nerve cells induce the activity of microglial cells again, the neurodegeneration is caught in a continuous vicious circle. In fact, it was reported that the activity of microglial cells is associated with various degenerative nerve diseases such as Alzheimer's disease, Parkinson's disease, Huntington's disease, Lou Gehrig's disease, Creutzfeldt-Jakob disease (CJD), multiple sclerosis, etc.

As such, considering the importance of the neuroinflammatory response in neuro-degenerative diseases, it is possible to treat neuroinflammation and neuro-degenerative diseases that may develop therefrom by reducing a level of expression of proinflammatory mediators in such microglial cells.

Meanwhile, *Portulaca grandiflora* Hook. is an annual herbaceous plant that belongs to the family Portulacaceae, is native to South America, and consists of approximately 40 species distributed all over the world. The whole plant of *Portulaca grandiflora* Hook. is referred to as *Scutellaria rivularis*, which has been used as medicine. It was reported that alfatoxin B1 and cyclophosphamide which are main components of *Portulaca grandiflora* Hook. have an anti-mutagenesis effect in rodents (Liu et al., Zhongguo Zhong Yao Za Zhi, 1990, 640, 617-622). However, there is no known use of *Portulaca grandiflora* Hook. in preventing or treating neuroinflammation or neuro-degenerative diseases.

DISCLOSURE

Technical Problem

The present inventors have endeavored to conduct much research in order to develop a method capable of preventing or treating dementia, and found that a *Portulaca grandiflora* Hook. extract or a fraction thereof inhibits a neuroinflammatory response and also has an effect of increasing and improving memory and the ability to learn. Therefore, the present invention has been completed based on the facts.

Technical Solution

An object of the present invention is to provide a pharmaceutical composition containing a *Portulaca grandiflora* Hook. extract or a fraction thereof as an active ingredient for preventing or treating neuroinflammation or neuro-degenerative diseases.

Another object of the present invention is to provide a food composition containing a *Portulaca grandiflora* Hook. extract or a fraction thereof as an active ingredient for preventing or ameliorating neuroinflammation or neuro-degenerative diseases.

Still another object of the present invention is to provide a composition containing a *Portulaca grandiflora* Hook. extract or a fraction thereof as an active ingredient for increasing and improving memory and the ability to learn.

Advantageous Effects

A *Portulaca grandiflora* Hook. extract or a fraction thereof according to the present invention inhibits expression of inflammation-related factors such as NO, $PGE_2$, iNOS and/or COX-2 genes or proteins without any side effects, since the extract or the fraction is derived from a natural product which has been used as a natural medicinal ingredient. Also, the *Portulaca grandiflora* Hook. extract or the fraction thereof according to the present invention can be useful in preventing or treating neuroinflammation or neuro-degenerative diseases since the extract or the fraction has an excellent effect in increasing and improving memory and the ability to learn.

DESCRIPTION OF DRAWINGS

FIGS. 5A and 5B are diagrams showing inhibitory effects on expression of COX-2 proteins and mRNA in BV-2 microglial cells when treated with the *Portulaca grandiflora* Hook. methanol extract.

FIG. 6 is a diagram showing an inhibitory effect on expression on β-CTF in a SH-SY5Y nerve cell line when treated with the *Portulaca grandiflora* Hook. methanol extract.

FIG. 9A to FIG. 9D are diagrams showing effects of the *Portulaca grandiflora* Hook. extract or the fraction thereof on improvement of working memory using a Y-maze test in a scopolamine-induced memory impairment model.

FIGS. 10A to 10D are diagrams showing effects of the *Portulaca grandiflora* Hook. extract or the fraction thereof on an improvement of memory and the ability to learn using a passive avoidance test.

BEST MODE

Figure 1:
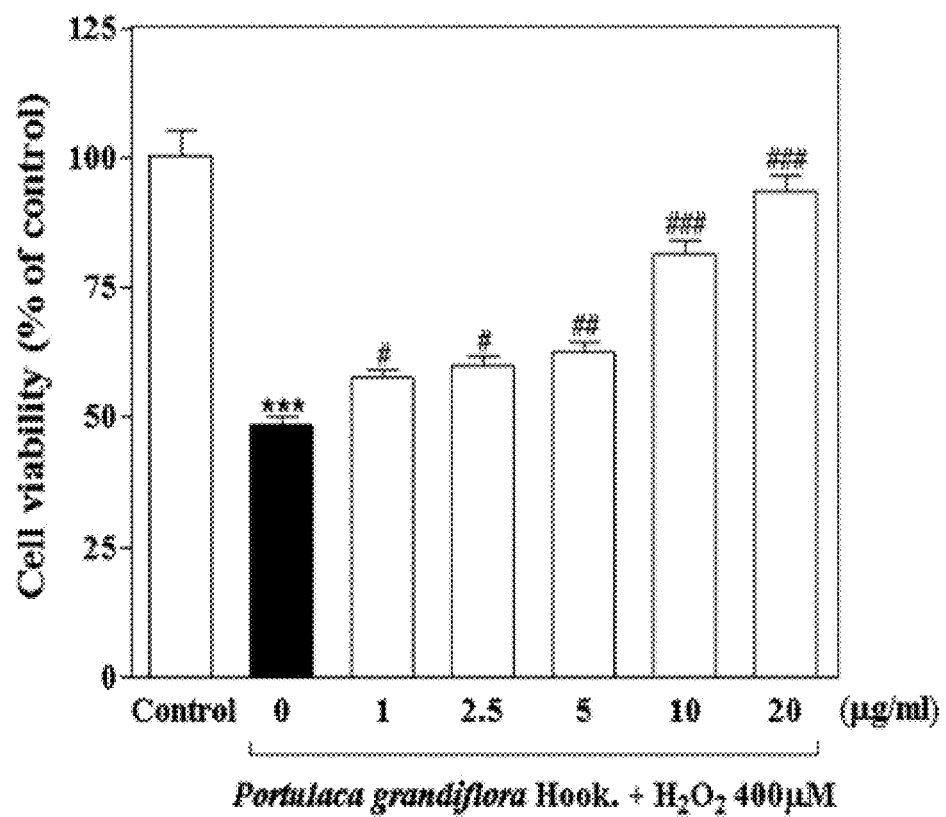
FIG. 1 is a diagram showing a protective effect on cerebral nerve cells in an SH-SY5Y nerve cell line when treated with a *Portulaca grandiflora* Hook. methanol extract.

To achieve the above objects, according to one aspect of the present invention, there is provided a pharmaceutical composition containing a *Portulaca grandiflora* Hook. extract or a fraction thereof as an active ingredient for preventing or treating neuroinflammation or neuro-degenerative diseases.

Specifically, the pharmaceutical composition for preventing or treating neuroinflammation or neuro-degenerative diseases according to the present invention may include a *Portulaca grandiflora* Hook. extract and/or a fraction thereof.

In the present invention, "*Portulaca grandiflora* Hook." is an annual herbaceous plant which belongs to the family Portulacaceae, is native to South America, and consists of approximately 40 species distributed all over the world. Stems of *Portulaca grandiflora* Hook. are fleshy in a cylindrical shape and red in color, grows supine, often branching from the base, and extend to a length of up to 30 cm for big stems. Leaves are fleshy and linear, and have no hair, and a large quantity of white hair grows from an axilla. One or two or more flowers are often gathered at the end of the stem. Red or white flowers bloom in summer, and have two floral cups in a wide oval shape and five petals in an obovoid shape with a pointed end. Also, the whole plant of *Portulaca grandiflora* Hook. is referred to as *Scutellaria rivularis*, which has been used as medicine.

In the present invention, the term "*Portulaca grandiflora* Hook. extract" refers to an extract obtained by extracting *Portulaca grandiflora* Hook. The *Portulaca grandiflora* Hook. extract is obtained by extracting ground parts of *Portulaca grandiflora* Hook. at an extraction temperature of 20 to 100° C., preferably room temperature, for an extraction period of approximately 12 hours to 4 days, preferably 3 days, using a polar solvent such as water, a lower alcohol having 1 ($C_1$) to 4 ($C_4$) carbon atoms (for example, methanol, ethanol, and butanol), or a mixed solvent thereof having a mixing ratio of approximately 1:0.1 to 1:10 as an elution solvent. Here, the volume of the polar solvent or the mixed solvent reaches approximately 2 to 20 times, preferably approximately 3 to 5 times of the dry weight of the ground parts, and the extraction is performed using an extraction method such as hot water extraction, cold extraction, reflux cooling extraction, or ultrasonic extraction, etc. For example, any methods of extracting a substance which has an activity to prevent or treat neuroinflammation or neuro-degenerative diseases may be used without limitation. Preferably, the *Portulaca grandiflora* Hook. extract may be a product obtained by extracting *Portulaca grandiflora* Hook. 1 to 5 times using cold extraction, filtering the resulting extract under vacuum and concentrating the filtered extract at 20 to 100° C., preferably room temperature under vacuum in a vacuum rotary evaporator to obtain a *Portulaca grandiflora* Hook. crude extract dissolved in water, a lower alcohol or a mixed solvent thereof. Types of extracts may be limited as long as the extracts may have an activity to prevent or treat neuroinflammation or neuro-degenerative diseases according to the present invention. For example, the extract may include all of an extract, a diluted or concentrated solution of the extract, a dry matter obtained by drying the extract, or a crude purified product or purified product thereof. The *Portulaca grandiflora* Hook. extract may be extracted from various organs of natural, hybrid, and modified plants, and may, for example, be extracted from roots, aerial parts, stems, flowers, branches, leaves, fruits, or plant tissue cultures, etc.

In the present invention, the term "fraction" refers to a product obtained by a fractionation method of separating a certain component or a certain group from a mixture including various components. The *Portulaca grandiflora* Hook. fraction of the present invention may be obtained by suspending the *Portulaca grandiflora* Hook. extract, and fractionating the extract into a polar solvent fraction and a non-polar solvent fraction using a polar solvent such as water, methanol, ethanol, etc., or a non-polar solvent such as hexane, ethyl acetate, etc. Specifically, a *Portulaca grandiflora* Hook. fraction may be obtained by suspending the *Portulaca grandiflora* Hook. crude extract in distilled water, etc., adding a polar or non-polar solvent such as water, an alcohol having 1 ($C_1$) to 4 ($C_4$) carbon atoms, chloroform, ethyl acetate, hexane, butanol or a mixed solvent thereof at a volume of approximately 1 to 100 folds, preferably approximately 1 to 5 folds of the suspension, and extracting and separating a polar or non-polar solvent-soluble layer 1 to 10 times, preferably 2 to 5 times.

Also, the fraction of the present invention may be obtained by further carrying out a conventional fractionation process (Harborne J. B. *Plant Pathology*, 1998, 3rd Ed. p 6-7). For example, fractions obtained by passing the *Portulaca grandiflora* Hook. extract according to the present invention through an ultrafiltration membrane having a certain molecular weight cut-off value, and active fractions obtained through various purification methods further carried out such as separation by various types of chromatography (designed for separation in response to the size, electric charges, hydrophobicity, or affinity) are also included in the *Portulaca grandiflora* Hook. fraction according to the present invention.

The active fraction is a fraction having higher physiological activity, which is separated from the fraction, and thus referred to as an active portion or an effective fraction. A certain active fraction having higher activity may be prepared by separating active components from a fraction, in which various components obtained through a conventional fractionation process such as systematic fractionation, depending on properties of the active components, using concentration-gradient column chromatography, etc. The column chromatography using a filler selected from the group consisting of silica gel, Sephadex, LH-20, ODS gel, RP-18, polyamide, Toyopearl, and an XAD resin may be performed to separate and purify the active fraction. When necessary, the column chromatography may be performed several times using a proper filler, but the present invention is not limited thereto. The solvent, rate or time generally used in the related art is applicable to an elution solvent, an elution rate and an elution time in use of the chromatography.

In one exemplary embodiment of the present invention, the resulting *Portulaca grandiflora* Hook. methanol extract is suspended by adding distilled water thereto, and ethyl acetate, butanol or water is added to obtain an ethyl acetate fraction, a butanol fraction or a water fraction, respectively (Example 1 and Example 2).

The *Portulaca grandiflora* Hook. extract or fraction thereof according to the present invention may be used for the purpose of preventing or treating neuroinflammation or neuro-degenerative diseases that may develop therefrom by inhibiting expression of nitrogen monoxide (NO), prostaglandin ($PGE_2$), iNOS and/or COX-2 genes or proteins known to be inflammation-related factors.

In the present invention, the term "neuroinflammation" generally refers to all types of inflammatory responses provoked in the nervous system, that is, nerve cells, nerve tissues, etc. The term encompasses situations in which microglial cells that are immunocytes present in the central nervous system may be activated due to various exogenous and endogenous substances to produce and release substances such as inflammatory cytokines TNF-α and IL-1β, nitrogen monoxide, prostaglandin, superoxide, etc. It is known that the production of such substances provokes immune responses in the short run, but the excessive or continuous production of the substances induces the death of neighboring nerve cells to cause neurodegeneration.

In one experimental embodiment of the present invention, it was found that the *Portulaca grandiflora* Hook. extract or fraction thereof is effective for preventing or treating neuroinflammation by confirming that the extract or fraction inhibits a level of expression of NO, $PGE_2$, iNOS and COX-2 proteins or mRNA known to be inflammation-related factors without causing toxicity to nerve cells (Experimental Example 2).

Also, the *Portulaca grandiflora* Hook. extract or fraction thereof according to the present invention may be used for the purpose of preventing or treating neuro-degenerative diseases by inhibiting expression of β-CTF and β-secretase (BACE1) known to be Alzheimer's disease-related enzymes.

In the present invention, the term "neuro-degenerative disease" generally refers to all types of diseases that cause various symptoms with a degenerative change in nerve cells of the central nervous system, and particularly includes impaired cognitive function, ability to learn or memory, or neurodegenerative disorders which are accompanied with the neuroinflammatory response. Representative neuro-degenerative diseases according to the present invention include dementia, Alzheimer's disease, Parkinson's disease, Huntington's disease, Lou Gehrig's disease (amyotrophic lateral sclerosis, ALS), Creutzfeldt-Jakob disease (CJD), stroke, multiple sclerosis, cognitive impairment, learning difficulties, memory impairment, etc.

Among theses, Alzheimer's disease (AD) is a disease that has emerged as the most important issue in senile dementia, and is known to be caused by intracerebral accumulation of amyloid beta (Aβ) and hence occurrence of neurotoxicity. The Aβ is known to be formed due to successive actions of an amyloid precursor protein (APP) with membrane proteases such as β-secretase 1 (BACE1) and γ-secretase. Therefore, it is apparent that Alzheimer's disease may be prevented or treated by inhibiting the expression of the BACE1 protein.

In one experimental embodiment of the present invention, it was found that the *Portulaca grandiflora* Hook. extract or fraction thereof has an effect of preventing or treating neuro-degenerative diseases by confirming that the extract or fraction inhibits a level of expression of proteins or mRNA of β-secretase-cleaved carboxyl-terminal fragment (β-CTF) and beta-secretase 1, beta-site APP-cleaving enzyme 1 (BACE1) known to be Alzheimer's disease-related genes (Experimental Example 3).

In the present invention, the term "preventing" or "prevention" refers to all types of actions to inhibit or delay the onset of neuroinflammation or neuro-degenerative diseases upon administration of the composition, and the term "treating" or "treatment" refers to all types of actions to improve or benefit symptoms caused by the neuroinflammation or neuro-degenerative diseases using the composition.

A pharmaceutical composition including the *Portulaca grandiflora* Hook. extract or fraction thereof according to the present invention may further include a carrier, an excipient, or a diluent which is suitable for general use in preparation of the pharmaceutical composition. In this case, the *Portulaca grandiflora* Hook. extract or fraction thereof included in the composition is not particularly limited, but may be included at a content of 0.001% by weight to 99% by weight, preferably 0.01% by weight to 50% by weight, based on the total weight of the composition.

The pharmaceutical composition may be prepared into any one formulation selected from the group consisting of a tablet, a pill, a powder, a granule, a capsule, a suspension, a liquid for internal use, an emulsion, a syrup, a sterile aqueous solution, a non-aqueous solvent, a suspension, an emulsion, a freeze-drying agent, and a suppository, and also prepared into various formulations for oral or parenteral administration. When formulated, the composition may be prepared using a diluent or excipient generally used in the related art, such as a filler, a bulking agent, a binder, a wetting agent, a disintegrating agent, a surfactant, etc. A solid preparation for oral administration includes a tablet, a pill, a powder, a granule, a capsule, etc. Such a solid preparation may be prepared by mixing at least one excipient, for example, starch, calcium carbonate, sucrose or lactose, gelatin and the like, with one or more compounds. Also, lubricants such as magnesium stearate, talc and the like may be used in addition to the simple excipients. A liquid preparation for oral administration includes a suspension, a liquid for internal use, an emulsion, a syrup, etc. In this case, the liquid preparation includes various excipients, for example, a wetting agent, a sweetening agent, a flavoring agent, a preservative, and the like in addition to the generally used simple diluents such as water, liquid paraffin, etc. A preparation for parenteral administration includes a sterile aqueous solution, a non-aqueous solvent, a suspension, an emulsion, a freeze-dried preparation, a suppository, etc. Propylene glycol, polyethylene glycol, and a vegetable oil such as olive oil, an injectable ester such as ethyl oleate, and the like may be used as the non-aqueous solvent and the suspending agent. Witepsol, Macrogol, Tween 61, cacao butter, laurin butter, glycerogelatin, and the like may be used as a base of the suppository.

According to another aspect, the present invention provides a method of preventing or treating neuroinflammation or neuro-degenerative diseases, which includes administering the pharmaceutical composition to a subject suspected to have neuroinflammation or neuro-degenerative diseases.

In the present invention, the subject suspected to have neuroinflammation or neuro-degenerative diseases refers to all types of animals including human beings who have suffered from the disease or may suffer from the disease. The subject may be effectively treated by administering the pharmaceutical composition of the present invention to the subject suspected to have neuroinflammation or neuro-degenerative diseases. The pharmaceutical composition and the neuroinflammation or neuro-degenerative diseases are as described above.

In the present invention, the term "administering" or "administration" means that the pharmaceutical composition of the present invention is administered to the subject suspected to have neuroinflammation or neuro-degenerative diseases using any suitable methods. In this case, the composition may be administered via various routes of oral or parenteral administration as long as the composition can reach target tissues using these routes of administration.

The pharmaceutical composition according to the present invention may be administered in a pharmaceutically effective amount.

In the present invention, the term "pharmaceutically effective amount" refers to an amount sufficient to treat a disease at a reasonable benefit/risk ratio applicable to any medical treatment. In this case, a level of the effective dose may be determined depending on the type, severity, age, and sex of a subject, the type of a disease, the activity of a drug, the sensitivity to the drug, an administration time, a route of administration, and a secretion rate, a therapeutic period, factors including drugs to be used together, and other factors well known in the field of medicine. The composition of the present invention may be administered as an individual therapeutic agent, or may be administered in combination with other therapeutic agents. In this case, the composition may be administered sequentially or concurrently with conventional therapeutic agents. And, the composition of the present invention may be administered in a single dose or a multiple dose. By considering all the above factors, it is important to administer the composition at a dose in which the maximum effect can be achieved without any side effects when administered at a minimum dose. Thus, the dose of the composition may be easily determined by those skilled in the related art.

The pharmaceutical composition according to the present invention is applicable to any subjects without any particular limitation as long as the pharmaceutical composition targets the neuroinflammation or neuro-degenerative diseases. For example, any of non-human animals such as a monkey, a dog, a cat, a rabbit, a guinea pig, a rat, a mouse, cattle, a sheep, a pig, a goat, etc., human beings, birds, and fishes may be used. The pharmaceutical composition may be parenterally, subcutaneously, intraperitoneally, intrapulmonarily and intranasally administered, and may be administered using a proper method including intralesional administration for local treatment, when necessary. A preferred dose of the pharmaceutical composition according to the present invention may vary depending on the condition and weight of a subject, the severity of a disease, the shape of a drug, a route of administration, and an administration period, but may be properly chosen by those skilled in the related art. For example, the pharmaceutical composition may be orally, intrarectally or intravenously administered, or may be administered by intramuscular, subcutaneous, endocervical or intracerebrovascular injection, but the present invention is not limited thereto.

The total daily dose of the composition suitable for use may be determined by prescription within the scope of medical judgment. In this case, the composition may be generally administered at a dose of 0.001 to 1,000 mg/kg, preferably 0.05 to 200 mg/kg, more preferably 0.1 to 100 mg/kg once or several times a day.

According to still another aspect, the present invention provides a food composition containing the *Portulaca grandiflora* Hook. extract or fraction thereof as an active ingredient for preventing or ameliorating neuroinflammation or neuro-degenerative diseases.

The *Portulaca grandiflora* Hook., and the extract and fraction thereof, and the neuroinflammation or neuro-degenerative diseases are as described above.

In the present invention, the term "ameliorating" or "amelioration" refers to all types of actions to improve or benefit the symptoms of a subject who has developed or is suspected to have a disease such as neuroinflammation or neuro-degenerative diseases, which are prevented or treated using the composition including the *Portulaca grandiflora* Hook. extract or fraction thereof as an active ingredient.

Specifically, the *Portulaca grandiflora* Hook. extract or fraction thereof according to the present invention may be added to the food composition for the purpose of preventing or ameliorating neuroinflammation or neuro-degenerative diseases.

The food composition according to the present invention may be included in the form of a pill, a powder, a granule, an infusum, a tablet, a capsule, or a solution. Types of foods to which the *Portulaca grandiflora* Hook. extract or fraction thereof according to the present invention may be added are not particularly limited, and include, for example, various drinks, gums, tea, vitamin complex, health food supplements, etc.

In addition to the *Portulaca grandiflora* Hook. extract or fraction thereof, other components may be added to the food composition, and types of the other components are not particularly limited. For example, like conventional foods, various herbal extracts, sitologically acceptable auxiliary food additives, or natural carbohydrates may be included as additional components, but the present invention is not limited thereto.

The "auxiliary food additive" refers to a component that may be auxiliarily added to foods, and thus may be added to prepare health functional foods for individual formulations, and may be properly selected and used by those skilled in the related art. Examples of the auxiliary food additive include various nutrients, vitamins, minerals (electrolytes), flavoring agents such as synthetic and natural flavoring agents, coloring agents and fillers, pectic acid and salts thereof, alginic acid and salts thereof, organic acids, protective colloid thickening agents, pH regulators, stabilizing agents, preservatives, glycerin, alcohols, carbonating agents used for carbonated drinks, etc., but types of the auxiliary food additives according to the present invention are not limited to the above listed examples of the auxiliary food additive.

Examples of the natural carbohydrates include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. In addition to the above-listed flavoring agents, natural flavoring agents (thaumatin, etc.), Stevia extracts (rebaudioside A, glycyrrhizin, etc.), and synthetic flavoring agents (saccharin, aspartame, etc.) may be used as the flavoring agent.

The health functional food may be included in the food composition according to the present invention. The "health functional food" refers to a food which is prepared and processed in the form of a tablet, a capsule, a powder, a granule, a liquid, and a pill using crude materials or components which have functionality beneficial to the human body. Here, the term "functionality" refers to a situation in which nutriments are regulated with respect to the structure and function of the human body, or an effect useful for health care such as a physiological effect is achieved. The health functional food according to the present invention may be prepared using methods generally used in the related art, and may be prepared by adding raw materials and components which are generally added in the related art in the preparation of the health functional food. Also, the health functional food has advantages in that the health functional food has no side effects which may occur upon long-term use of drugs since the food is used as a raw material unlike common drugs, and may be highly portable.

An amount of the mixed active ingredients may be properly determined depending on the purpose of use (prophylactic, heath or therapeutic treatment). In general, the *Portulaca grandiflora* Hook. extract or fraction thereof according to the present invention may be added at an amount of 1 to 50% by weight, preferably 5 to 10% by weight, based on the total amount of the raw material composition upon preparation of foods, but the present invention is not limited thereto. However, the *Portulaca grandiflora* Hook. extract or fraction thereof according to the present invention may be used at a content less than or equal to this amount when used for a long time for the purpose of health or hygiene or the purpose of regulating the health.

Types of the food are not particularly limited. Examples of the food to which the above-described materials may be added may include meat, sausage, bread, chocolate, candies, snacks, confectionery, pizza, ramen, other noodles, gum, dairy products including ice cream, various soups, beverages, tea, drinks, alcohol beverages, and vitamin complex, and may include all types of health functional foods in a conventional aspect.

According to yet another aspect, the present invention provides a composition containing the *Portulaca grandiflora* Hook. extract or fraction thereof as an active ingredient for increasing and improving memory and the ability to learn.

The *Portulaca grandiflora* Hook., and the extract and fraction thereof are as described above.

According to one experimental embodiment of the present invention, the *Portulaca grandiflora* Hook. extract or fraction thereof is administered in a mouse model. As a result, it was confirmed that the *Portulaca grandiflora* Hook. extract or fraction thereof has an effect of increasing working memory in a Y-maze test and an effect of increasing memory in a passive avoidance test. Therefore, the *Portulaca grandiflora* Hook. extract or fraction thereof according to the present invention may be used to increase the memory and the ability to learn. In this case, the composition may be a pharmaceutical composition, a sanitary aid composition, or a food composition.

Also, the present invention provides a use of the *Portulaca grandiflora* Hook. extract or fraction thereof to prepare the pharmaceutical composition or the food composition for preventing, treating or ameliorating neuroinflammation or neuro-degenerative diseases.

In addition, the present invention provides a use of the *Portulaca grandiflora* Hook. extract or fraction thereof to prepare the food composition for increasing or improving memory and the ability to learn.

Further, the present invention provides a method of increasing or improving memory and the ability to learn for a subject, which includes administering the *Portulaca grandiflora* Hook. extract or fraction thereof to the subject in need thereof.

[Mode for Invention]

Hereinafter, the configurations and effects of the present invention will be described in further detail with reference to examples thereof. However, it should be understood that the following examples are just preferred examples for the purpose of illustration only and is not intended to limit or define the scope of the invention.

1. Drugs and Reagents Amyloid beta$_{25\text{-}35}$ (A$\beta_{25\text{-}35}$), dimethyl sulfoxide (DMSO), 30% hydrogen peroxide (H$_2$O$_2$), a lipopolysaccharide, phosphoric acid, poly-D-lysine, 3-(4,5-dimethyl thiazol-2-yl)-2,5-diphenyl tetrazolium bromide (MTT), N-(1-naphthyl)ethylenediamine dihydrochloride, sulphanilamide, Tween-20, scopolamine, and anti-β-actin antibodies were purchased from Sigma Chemical Co. (St. Louis, Mo., USA). A Dulbecco's modified Eagle's medium (DMEM) was purchased from Hyclone (Logan, Utah, USA). A fetal bovine serum (FBS), 0.25% trypsin-EDTA, and a penicillin/streptomycin mixture were purchased from GIBCO-BRL (Grand Island, Nebr., USA). Rabbit anti-rabbit horseradish peroxidase-linked IgG antibodies were purchased from Cell Signaling (Boston, Mass., USA). Rabbit anti-APP, rabbit anti-BACE1, rabbit anti-COX-2 and rabbit anti-iNOS antibodies were purchased from Epitomics (Burlingame, Calif., USA), and a TRIZOL, cDNA synthesis kit was purchased from Invitrogen (MolecularProbes, OR, USA). A PGE$_2$ ELISA kit (Cayman, Mich., USA) was used herein. In addition, products of best quality were purchased and used as the reagents used in experiments.

2. Preparation of Laboratory Animals

Four-week-old ICR male mice (25 to 30 g) were provided by Koatech (Gyeonggi-do, Korea), and bred and adapted for at least a week in an animal breeding room in the college of Pharmacy at Sungkyunkwan University, and then used. Water and feed were freely supplied, and the temperature (23±2° C.), humidity (55±10%) and light/dark cycle (12 hours) were automatically controlled.

<Preparation of Aβ$_{25-35}$-Induced Dementia Model>

Aβ$_{25-35}$ was dissolved in saline having a final concentration of 1 mM, and activated at 37° C. for 5 days. Thereafter, the 4-week-old ICR male mice (25 to 30 g) were anesthetized with Entobar, and 6 nmol/3 μL of Aβ$_{25-35}$ was injected into the left ventricle using a stereotaxic apparatus. After the injection, the laboratory animals were stabilized under a constant temperature of 37° C. or more for recovery.

3. Cell Culture

Human neuroblastoma SH-SY5Y cells, SH-SY5Y Swedish transformant cells and mouse BV-2 microglial cells were cultured in a Dulbecco's modified eagle's medium (DMEM, Hyclone, Thermo, USA) supplemented with inactivated 10% fetal bovine serum (FBS) and an antibiotic. An incubator was maintained at a temperature of 37° C., and a mixed gas of 95% air and 5% CO2 was continuously supplied to match proper conditions for cell culture. The cells were cultured at a density of $2.5 \times 10^4$, $5 \times 10^5$, and $1 \times 10^6$ cells in 6-, 24- and 96-well plates before 24 hours of experiments. The concentration of hydrogen peroxide was set to 400 μM, and the concentration of LPS was set to 100 ng/ml. A *Portulaca grandiflora* Hook. methanol crude extract was dissolved in 100% DMSO, and used at a final concentration of 0.1% or less.

4. Statistical Processing

All experimental results were statistically processed using a one-way analysis of variance (ANOVA), and a significance test was performed at a level of $p<0.05$ or less using a Newman-Keuls test when the significance was tested.

Example 1: Preparation of *Portulaca Grandiflora* Hook. Methanol Extract

*Portulaca grandiflora* Hook. (Distribution No.: FBM016-068) collected in Yunnan, China and dried under the shade was distributed from the International Biological Material Research Center of Korea Research Institute of Bioscience and Biotechnology, and used. 300 g of dried *Portulaca grandiflora* Hook. was completely dried and ground. Then, 300 g of the *Portulaca grandiflora* Hook. was repeatedly extracted three times in 3 L of 95% methanol at a temperature of 85° C., concentrated under reduced pressure using a vacuum evaporator (EYELA, N-1000, Japan), and freeze-dried to obtain 90 g of a *Portulaca grandiflora* Hook. methanol crude extract.

Example 2: Preparation of *Portulaca Grandiflora* Hook. Fraction

Example 2-1: Preparation of *Portulaca Grandiflora* Hook. Ethyl Acetate Fraction 36.3 g of the *Portulaca grandiflora* Hook. methanol crude extract, which was obtained from 300 g of *Portulaca grandiflora* Hook. in the same manner as in Example 1, was suspended in 1 L of water, and then extracted twice with 1 L of ethyl acetate (EtAc) to obtain 8 g of an ethyl acetate-soluble fraction.

Example 2-2: Preparation of *Portulaca Grandiflora* Hook. Butanol Fraction

A water layer remaining after the fractionation in Example 2-1 was again extracted twice with 1 L of butanol (BuOH) to obtain 5.79 g of a butanol-soluble fraction.

Example 2-3: Preparation of *Portulaca Grandiflora* Hook. Water Fraction

A water layer remaining after the fractionation of the *Portulaca grandiflora* Hook. butanol-soluble fraction obtained in Example 2-2 was concentrated to obtain 20.55 g of a water fraction.

Each of the *Portulaca grandiflora* Hook. extract and fractions was treated with hot water, concentration under reduced pressure, and then used in experiments.

Experimental Example 1: Protective Effect of *Portulaca Grandiflora* Hook. Extract on Nerve Cells To check the viability of nerve cells (SH-SY5Y) through treatment with the *Portulaca grandiflora* Hook. extract, an MTT reduction assay was used. An MTT solution was added to each of wells of the 96-well plates undergoing the experiments at a final concentration of 0.5 mg/mL. The resulting mixture was reacted for 2 hours in an incubator, and the medium and the MTT solution were removed. DMSO was added thereto, and stirred. When DMSO was completely dissolved, the UV optical density was measured at 540 nm using a microplate reader (Molecular Device, USA).

The cell viability was calculated by applying the measured optical density value to the following Mathematical Equation 1 to calculate the.

$$\text{Cell Viability}(\%) = \frac{O.D. \text{ of Control} - O.D. \text{ of Experimental Group}}{O.D. \text{ of Control}} \times 100 \qquad \text{[Mathematical Equation 1]}$$

As a result, it was confirmed that the cell viability was remarkably reduced to 48% when the cells were treated with hydrogen peroxide alone without treatment with the *Portulaca grandiflora* Hook. extract, but that the cell viability increased in an extract dose-dependent manner when the cells were treated with the *Portulaca grandiflora* Hook. extract, indicating that the *Portulaca grandiflora* Hook. extract has a significant neuroprotective effect (FIG. 1).

Experimental Example 2: Anti-Inflammatory Effect of *Portulaca Grandiflora* Hook. Extract Experimental Example 2-1: Inhibitory Effect of *Portulaca Grandiflora* Hook. Extract on Generation of Nitrogen Monoxide (NO)

To check an anti-inflammatory effect of the *Portulaca grandiflora* Hook. extract, a production amount of NO that was an inflammatory mediator was quantitatively measured. Specifically, $2.5 \times 10^5$ BV-2 microglial cells were seeded in each well of a 24-well plate before 24 hours of experiments, and 100 ng/mL of a neuroinflammation inducer, LPS, and a different concentration of the *Portulaca grandiflora* Hook. extract prepared in Example 1 were added, and reacted for 24 hours in an incubator. Then, 50 μL of a Griess reagent (1% sulfonilamine/0.1% N-(1-naphtyl)-ethylenediamine dihydrochloride/5% phosphate) was added to each well, and then reacted for 15 minutes. Subsequently, an inhibitory effect on the neuroinflammatory response was measured at a wavelength of 540 nm using a microplate reader (Molecular Device, USA).

Figure 2:
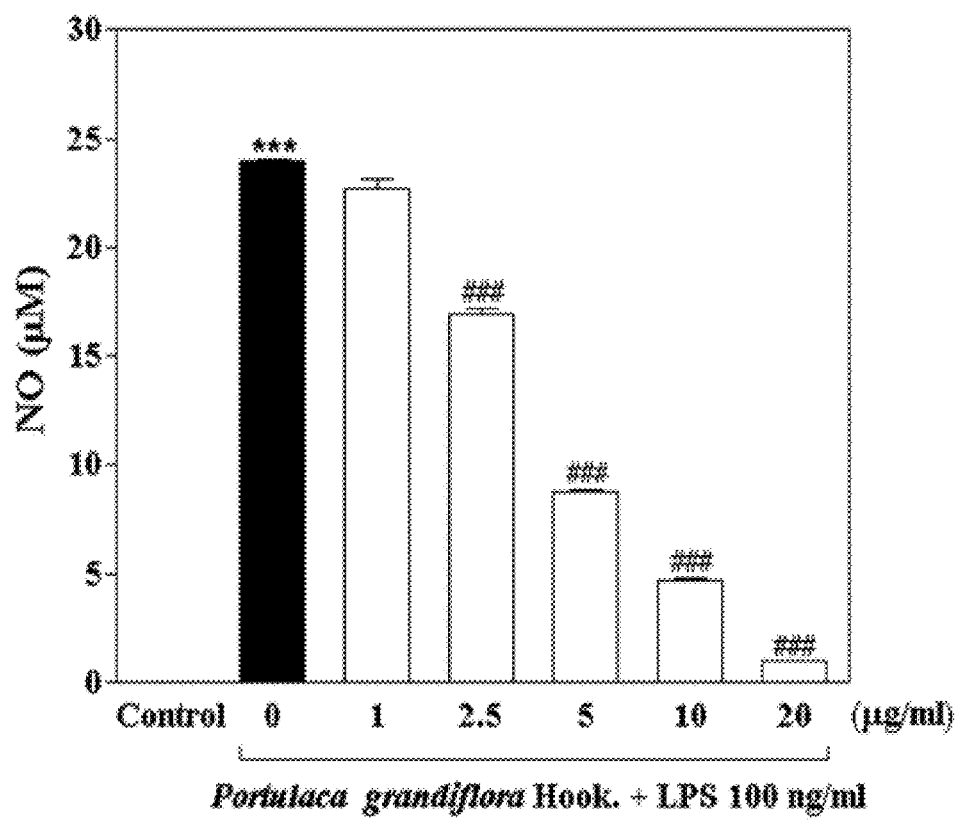
FIG. 2 is a diagram showing an inhibitory effect on generation of NO in a BV-2 microglial cells when treated with the *Portulaca grandiflora* Hook. methanol extract.

As a result, it was confirmed that a production amount of NO in the BV-2 microglial cells remarkably increased when the cells were treated with LPS, and that the production amount of NO remarkably increased by the LPS treatment was inhibited by the *Portulaca grandiflora* Hook. extract in a dose-dependent manner (FIG. 2).

Experimental Example 2-2: Inhibitory Effect of *Portulaca Grandiflora* Hook. Extract on Production of Prostaglandin E2 ($PGE_2$)

To check an anti-inflammatory effect of the *Portulaca grandiflora* Hook. extract, a production amount of $PGE_2$ that was an inflammatory mediator was quantitatively measured. Specifically, BV-2 microglial cells were seeded in each well of a 24-well plate at a density of $2.5 \times 10^5$ cells/mL before 24 hours of experiments, 100 ng/mL of a neuroinflammation inducer, LPS, and an increasing concentration of the *Portulaca grandiflora* Hook. extract prepared in Example 1 were added, and then reacted for 24 hours in an incubator. After 24 hours, a supernatant was collected from the wells treated with each concentration, and the collected cells were precipitated at 400 g for 3 minutes using a centrifuge. Subsequently, the concentration of the cells were determined using a $PGE_2$ ELISA kit, and the UV optical density was measured at 490 nm using a microplate reader (Molecular Device, USA). The $PGE_2$ production was calculated using a quantitative graph of the standard curve plotted for the measured optical density values.

Figure 3:
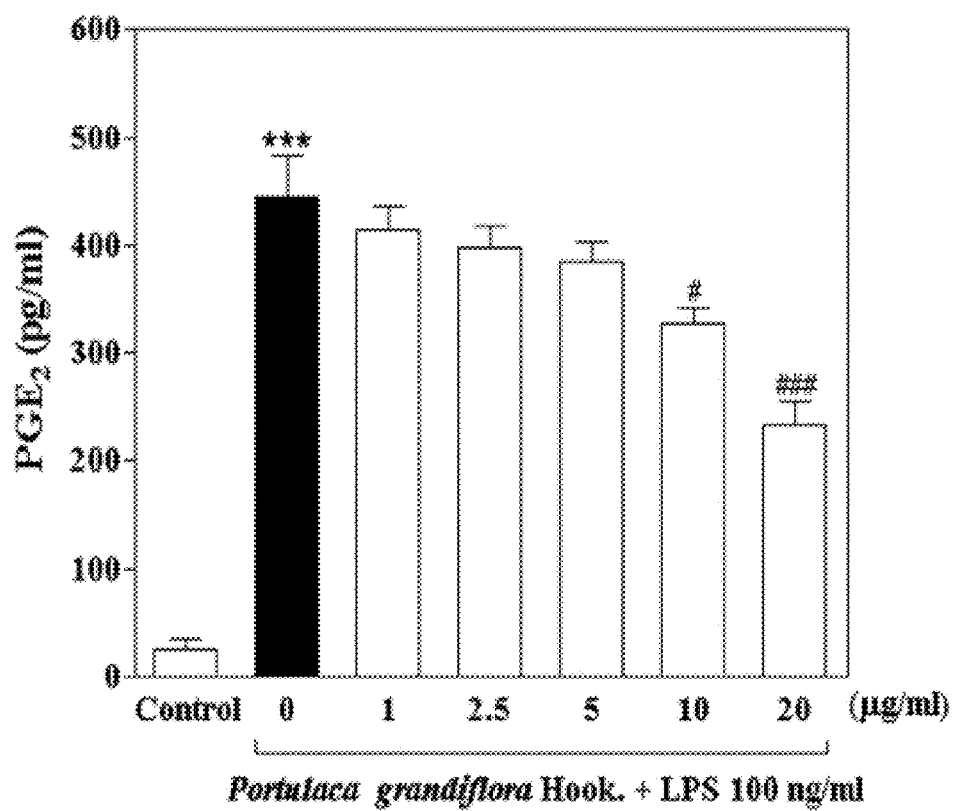
FIG. 3 is a diagram showing an inhibitory effect on generation of $PGE_2$ in BV-2 microglial cells when treated with the *Portulaca grandiflora* Hook. methanol extract.

As a result, it was confirmed that a production amount of $PGE_2$ in the BV-2 microglial cells remarkably increased when the cells were treated with LPS, and that the production amount of NO remarkably increased by the LPS treatment was inhibited by the *Portulaca grandiflora* Hook. extract in a dose-dependent manner (FIG. 3).

Experimental Example 2-3: Inhibitory Effect of *Portulaca Grandiflora* Hook. Extract on Expression of iNOS and COX-2 Proteins and mRNA For an identification test of expression of neuroinflammation-related proteins and mRNA in BV-2 microglial cells by the *Portulaca grandiflora* Hook. extract, Western blot and RT-PCR experiments were performed. The 6-well plate undergoing the experiments was pre-treated with the *Portulaca grandiflora* Hook. extract for 30 minutes, treated with LPS, and then reacted for 6 hours or 24 hours in an incubator. After 6 hours or 24 hours, a supernatant was collected from the wells treated with each concentration, and the collected cells were precipitated at 400 g for 3 minutes using a centrifuge, and washed with cold PBS. Thereafter, 100 µL of a Tper lysis buffer (Thermo, USA) was added thereto, and the cells were lysed for 30 minutes. The lysates were centrifuged at 10,000 g and 4° C. for 15 minutes using a centrifuge. After the centrifugation, the supernatant was stored at 70° C. until use as a sample for experiments. The proteins were quantitatively analyzed using a BCA quantitative analysis kit (Thermo, USA), eluted with 8% to 12% SDS gel, and transferred to a PVDF membrane. To check expression of the proteins, fluorescence development was performed using enhanced chemiluminescence (ECL). First, the membrane was reacted with 5% skimmed milk powder for an hour, labeled overnight with primary antibodies iNOS, COX-2 and β-actin at 4° C., washed five times with TTBS, and then labeled with horseradish peroxidase (HRP)-conjugated anti-rabbit and anti-mouse antibodies as secondary antibodies at room temperature for an hour. After the labeling, the membrane was washed five timed with TTBS for 10 minutes. Then, the washed membrane was developed on an X-ray film using ECL. The concentration was analyzed according to a quantitative analysis method using a quantitative analysis program (Fujifilm, Japan). Also, to check the mRNA expression, the full-length RNA was extracted using TRIZOL (Invitrogen), and RT-PCR was performed using a cDNA synthesis kit (Invitrogen). Primers for iNOS, COX-2 and β-actin were used in the RT-PCR. Sequences of the primers are listed in the following Table 1.

TABLE 1

| Genes | Forward primers | Reverse primers | Size (bp) of RT-PCR product |
|---|---|---|---|
| iNOS | 5'-CCCTTCCGAAGT TTCTGGCAGCAGC-3 (SEQ ID NO: 1) | 5'-GGCTGTCAGAGC CTCGTGGCTTTGG-3 (SEQ ID NO: 2) | 497 |
| COX-2 | 5'-TTGAAGACCAGG AGTACAGC-3 (SEQ ID NO: 3) | 5'-GGTACAGTTCCA TGACATCG-3 (SEQ ID NO: 4) | 324 |
| β-actin | 5'-AGCCATGTACGT AGCCATCC-3 (SEQ ID NO: 5) | 5'-GCTGTGGTGGTG AAGCTGTA-3 (SEQ ID NO: 6) | 222 |

Figure 4A:
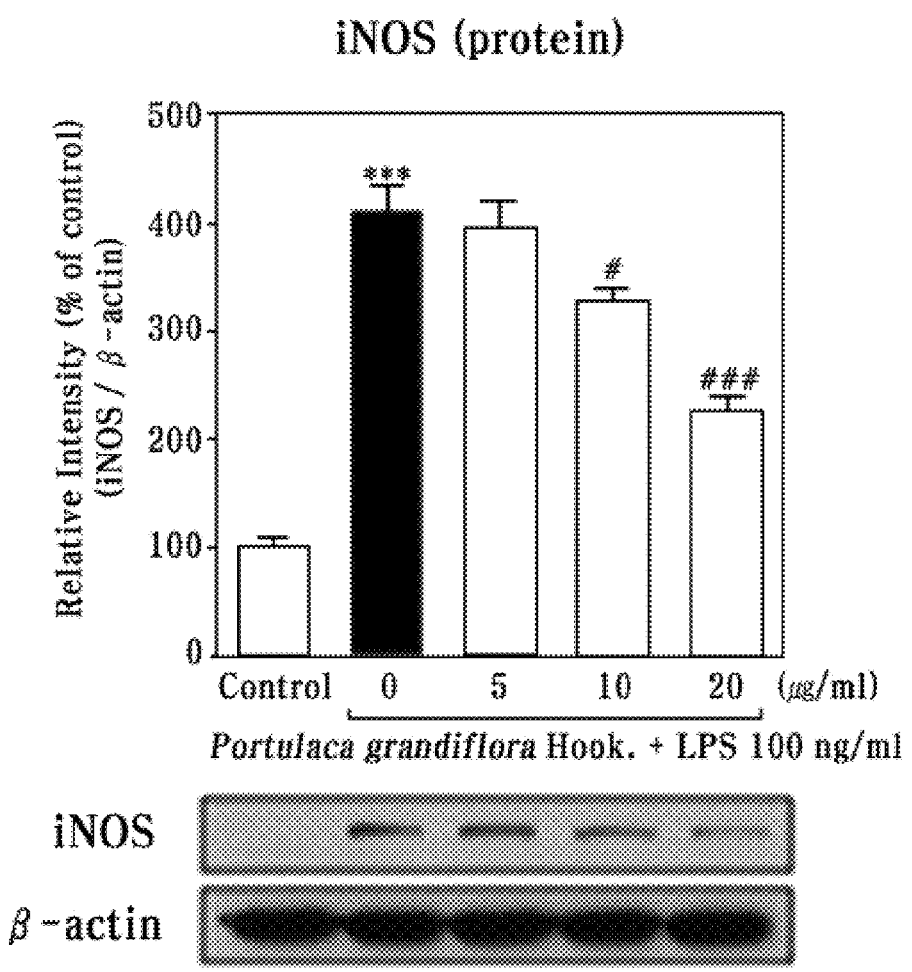
FIGS. 4A and 4B are diagrams showing inhibitory effects on expression of iNOS proteins and mRNA in BV-2 microglial cells when treated with the *Portulaca grandiflora* Hook. methanol extract.
Figure 4B:
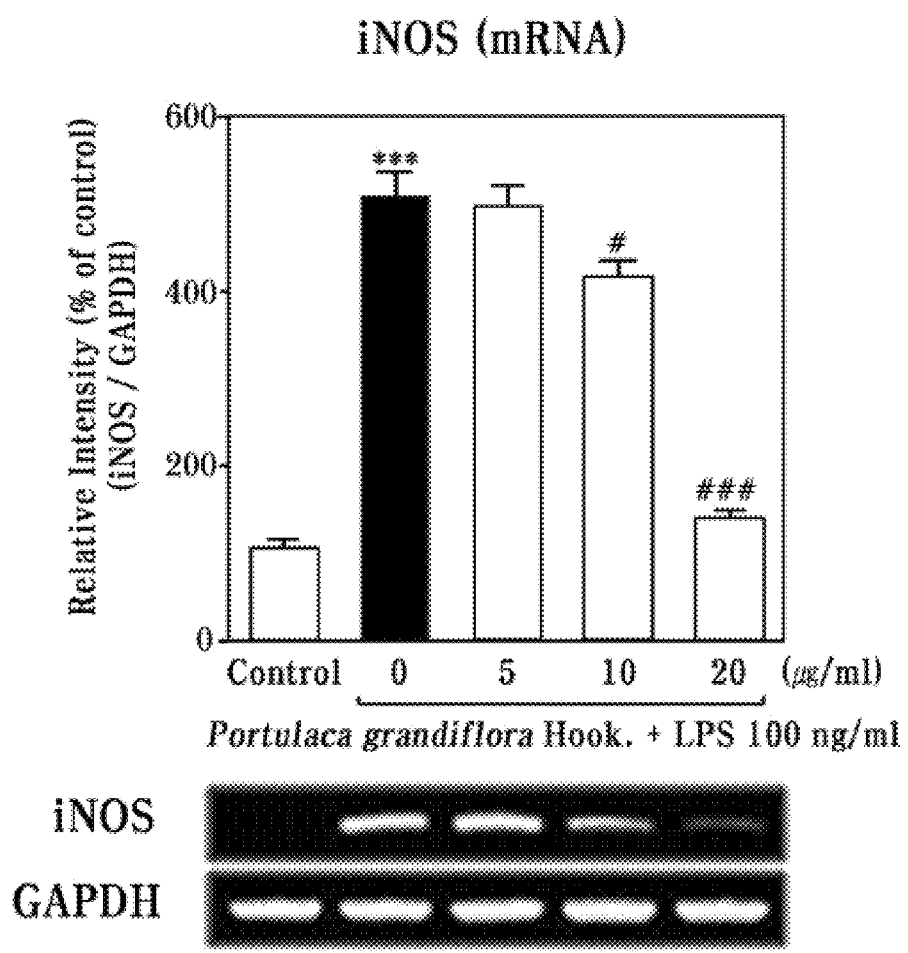

As a result, it was confirmed that the expression levels of iNOS and COX-2 proteins and mRNA remarkably increased through LPS treatment, but the expression levels of the proteins and mRNA remarkably decreased when the *Portulaca grandiflora* Hook. extract was administered (FIGS. 4 and 5).

Experimental Example 3: Inhibitory Effect of *Portulaca Grandiflora* Hook. Extract on Expression of Alzheimer's Disease-Related Genes and Proteins For an identification test of expression of dementia (Alzheimer's disease)-related proteins and mRNA in an SH-SY5Y Swedish transformant nerve cell line by the *Portulaca grandiflora* Hook. extract, Western blot and RT-PCR experiments were performed for β-CTF and BACE1, respectively. The 6-well plate undergoing the experiments was pre-treated with the *Portulaca grandiflora* Hook. extract for 24 hours, and then reacted in an incubator. After 24 hours, a supernatant was collected from the wells treated with each concentration, and the collected cells were precipitated at 400 g for 3 minutes using a centrifuge, and washed with cold PBS. Thereafter, 100 µL of a Tper lysis buffer (Thermo, USA) was added thereto, and the cells were lysed for 30 minutes. The lysates were centrifuged at 10,000 g and 4° C. for 15 minutes using a centrifuge. After the centrifugation, the supernatant was stored at 70° C. until use as a sample for experiments.

The proteins were quantitatively analyzed using a BCA quantitative analysis kit (Thermo, USA), eluted with 12.5% SDS gel, and transferred to a PVDF membrane. To check expression of the proteins, fluorescence development was performed using enhanced chemiluminescence (ECL). First, the membrane was reacted with 5% skimmed milk powder for an hour, labeled overnight with primary antibodies APP, β-CTF, BACE1 and β-actin at 4° C., washed five times with TTBS, and then labeled with horseradish peroxidase (HRP)- conjugated anti-rabbit and anti-mouse antibodies as secondary antibodies at room temperature for an hour. After the labeling, the membrane was washed five timed with TTBS for 10 minutes. Then, the washed membrane was developed on an X-ray film using ECL. The concentration was analyzed according to a quantitative analysis method using a quantitative analysis program (Fujifilm, Japan).

Meanwhile, to check the mRNA expression, the full-length RNA was extracted using TRIZOL (Invitrogen), and RT-PCR was performed using a cDNA synthesis kit (Invitrogen). Primers for BACE1 and β-actin were used in the RT-PCR. Sequences of the primers are listed in the following Table 2.

TABLE 2

| Gene | Forward primer | Reverse primer | Size (bp) of RT-PCR product |
|---|---|---|---|
| BACE1 | 5'-CATTGGAGGTAT CGACCACTCGCT-3 (SEQ ID NO: 7) | 5'-CCACAGTCTTCC ATGTCCAAGGTG-3 (SEQ ID NO: 8) | 624 |

As a result, it was confirmed that the level of expression of a β-secretase-cleaved carboxyl-terminal fragment (β-CTF) protein was inhibited by the treated *Portulaca grandiflora* Hook. extract in a dose-dependent manner (FIG. 6).

Figure 7A:
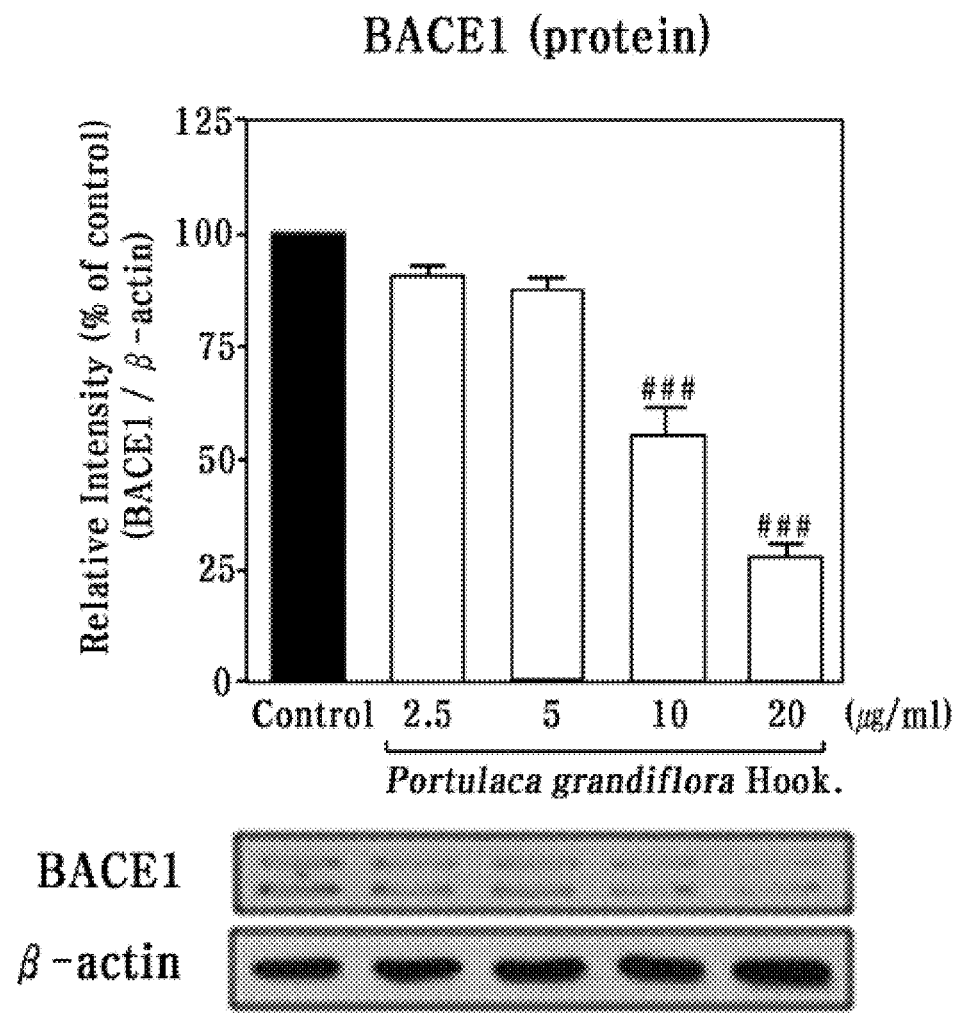
FIGS. 7A and 7B are diagrams showing inhibitory effects on expression of BACE1 in the SH-SY5Y nerve cell line when treated with the *Portulaca grandiflora* Hook. methanol extract.
Figure 7B:
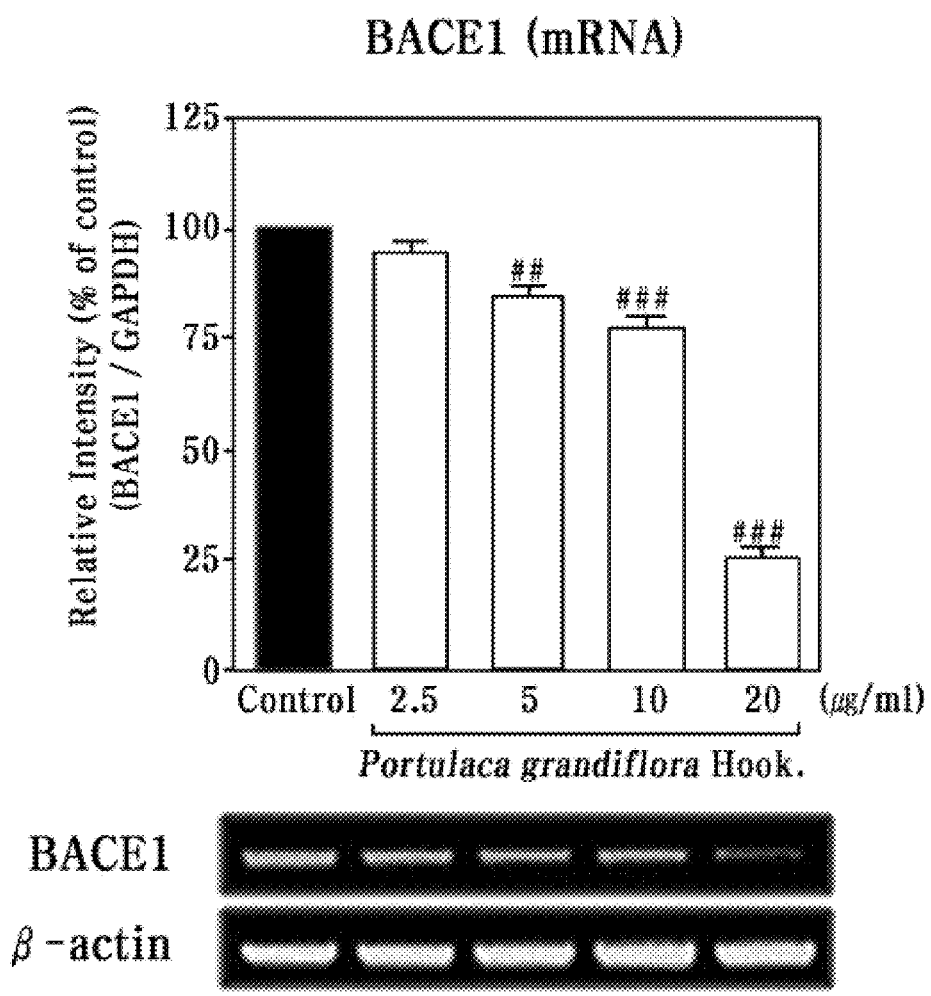
Figure 8A:
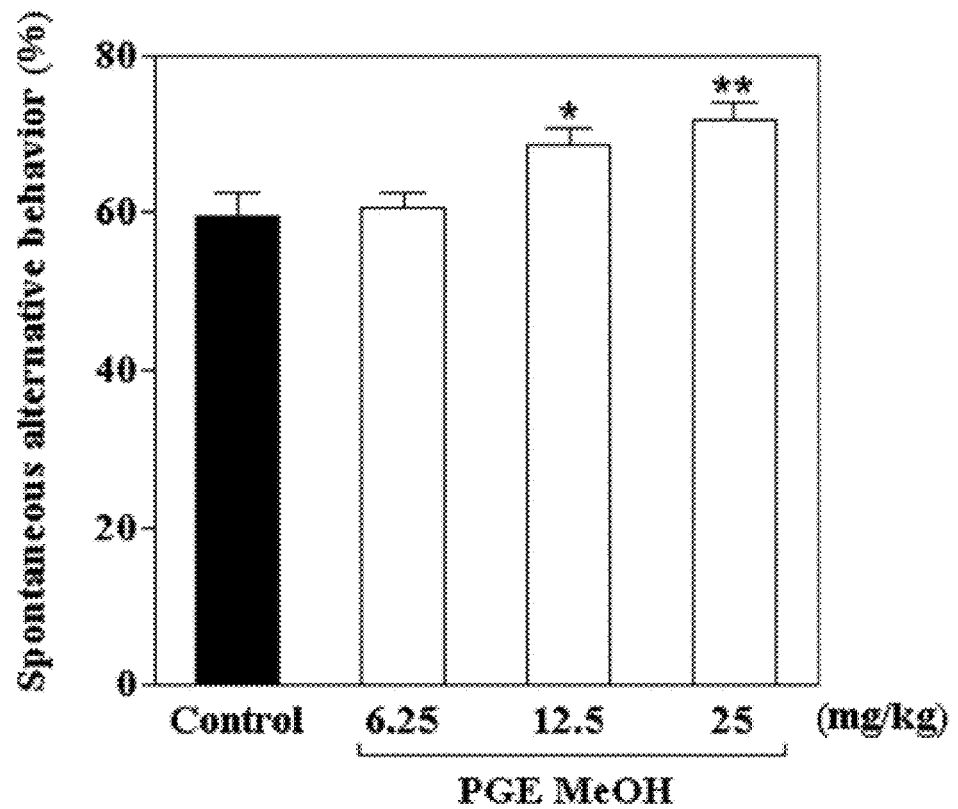
FIGS. 8A to 8D are diagrams showing effects of the *Portulaca grandiflora* Hook. extract or the fraction thereof on an improvement of working memory using a Y-maze test.
Figure 8B:
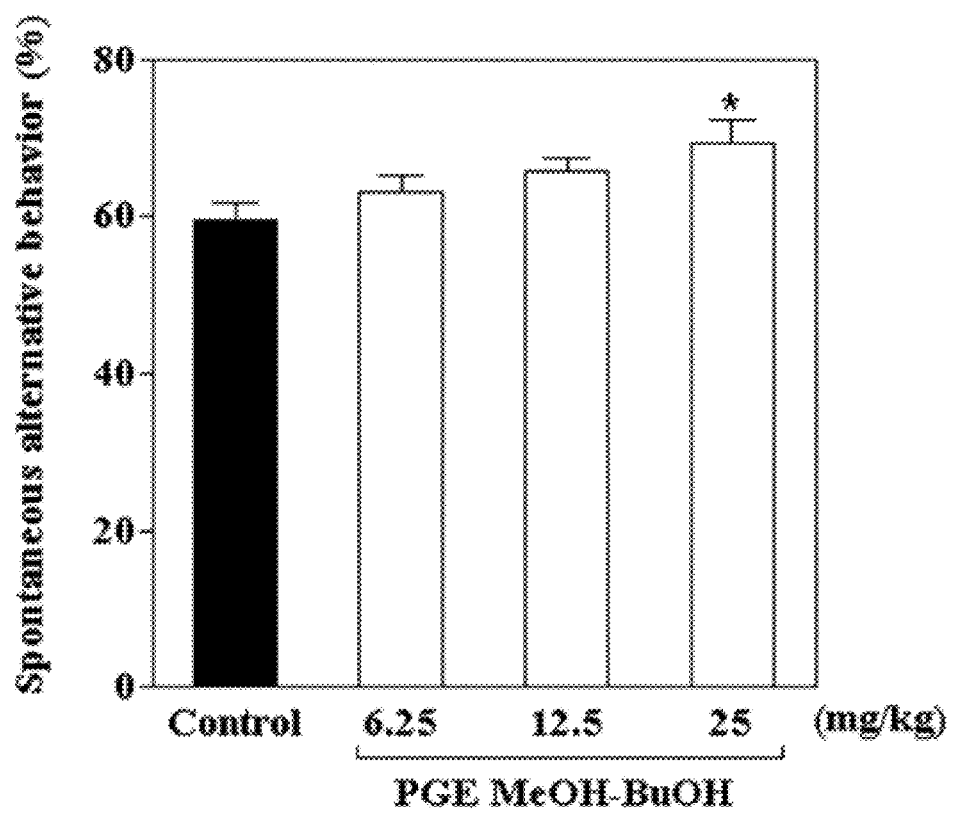
Figure 8C:
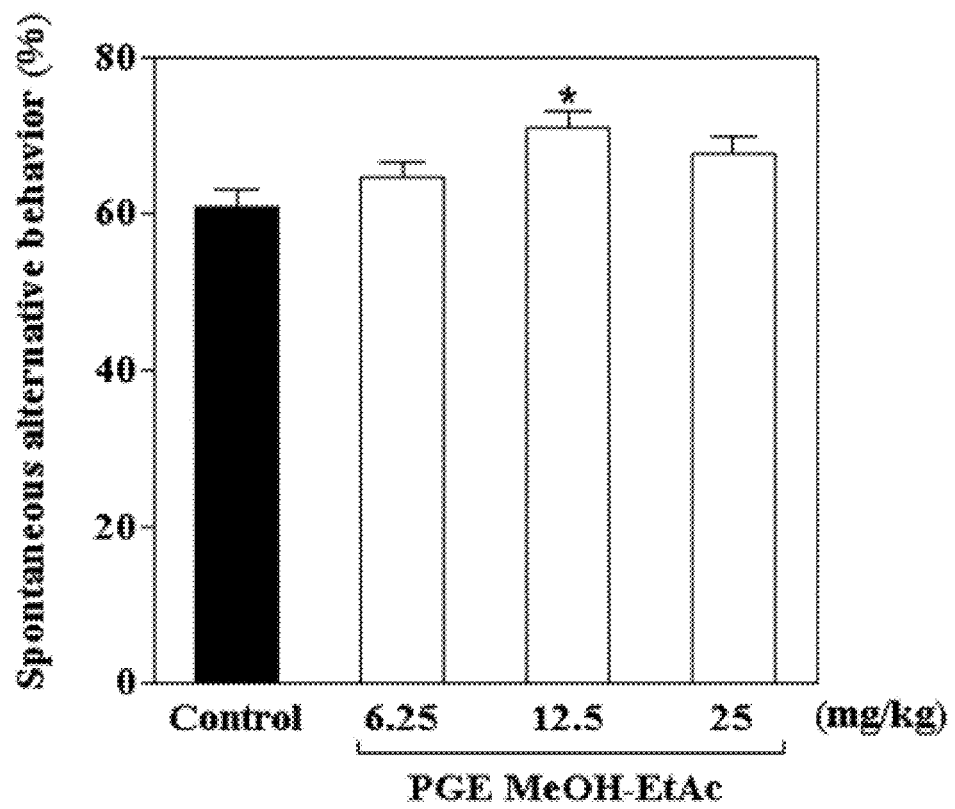
Figure 8D:
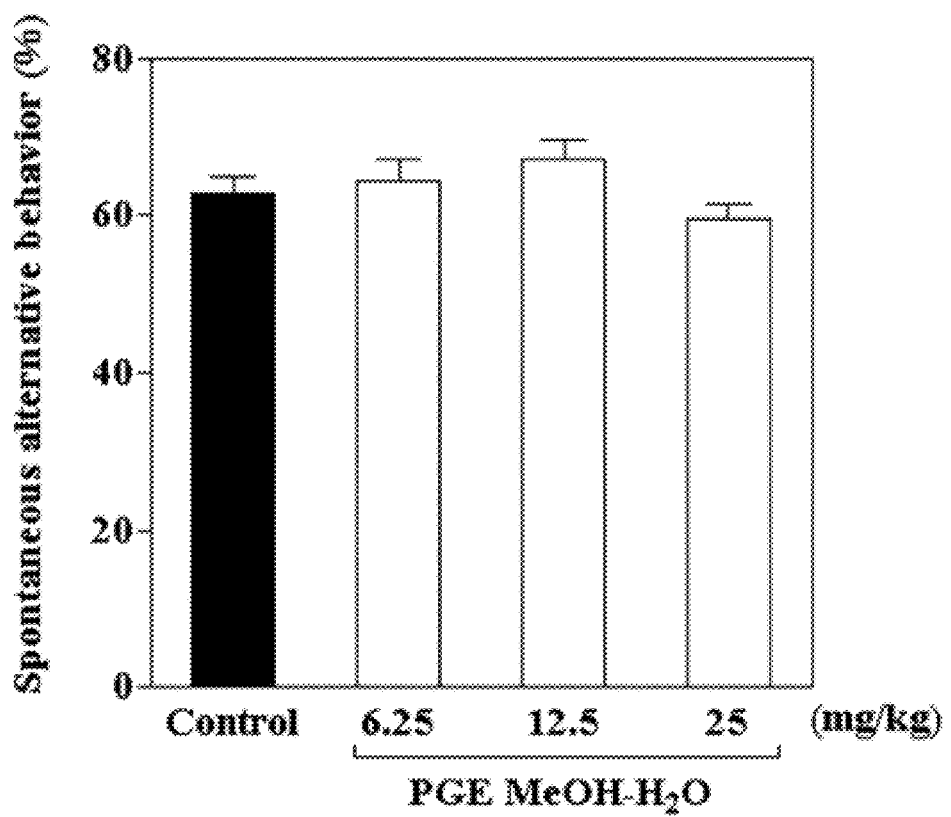
Figure 9A:
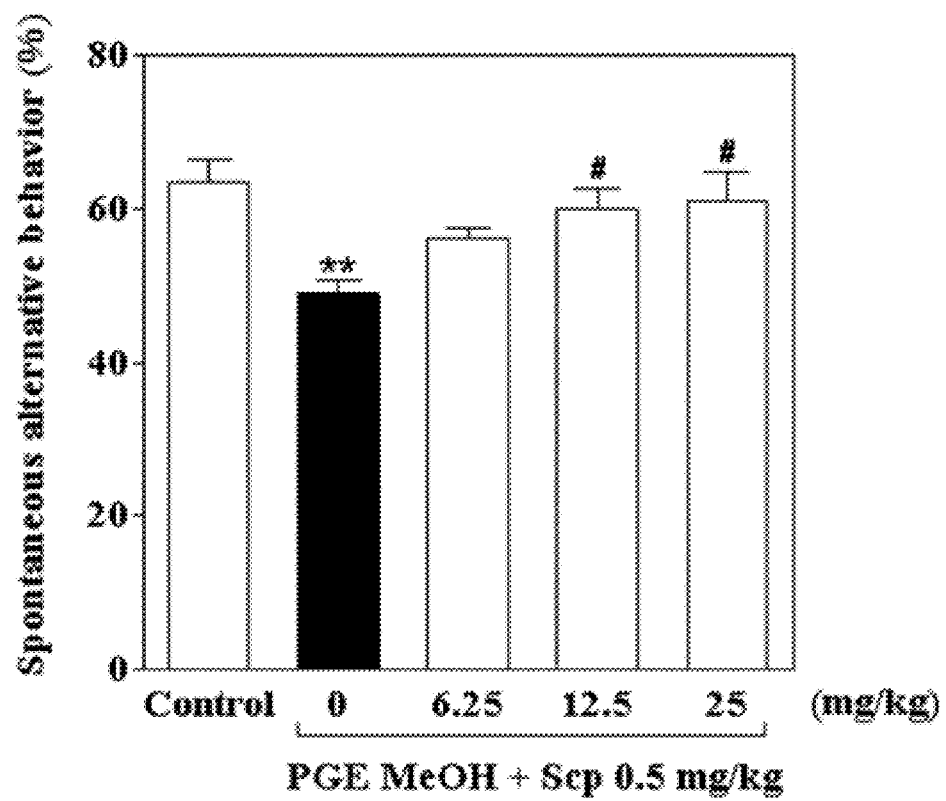
Figure 9B:
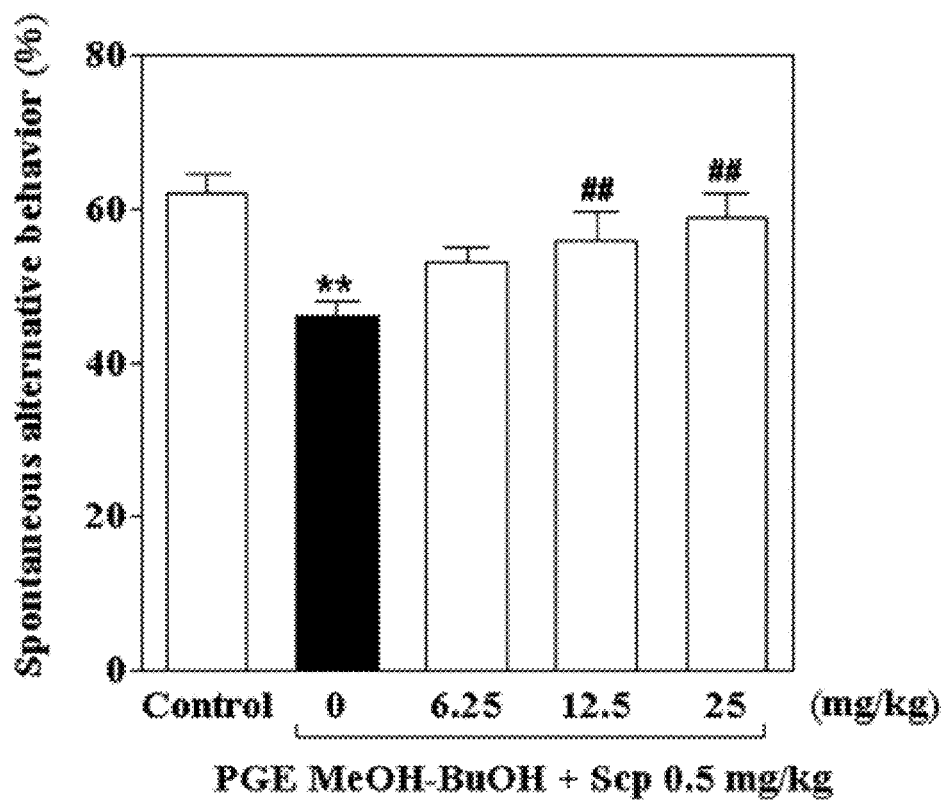
Figure 9C:
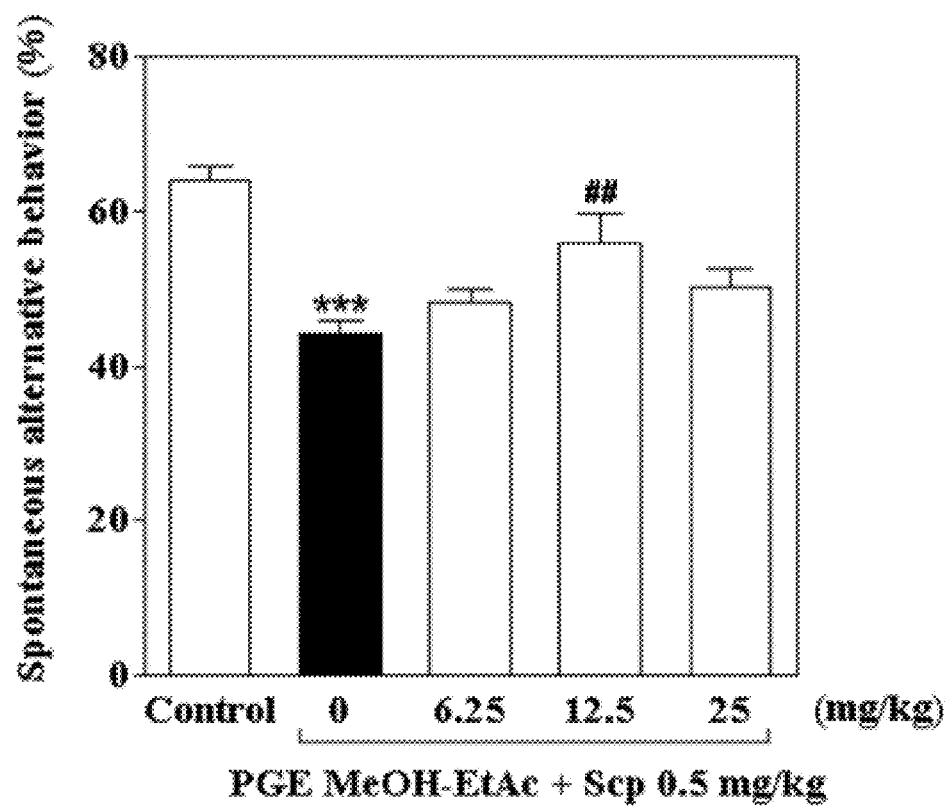
Figure 10B:
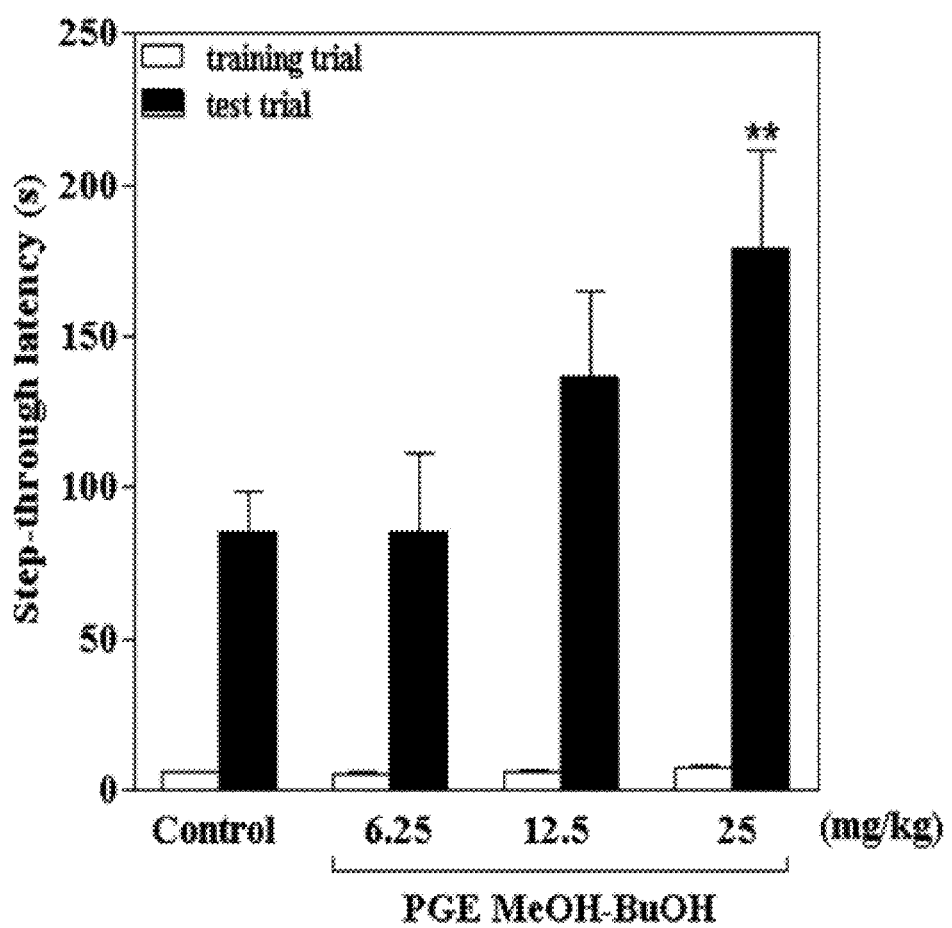
Figure 11A:
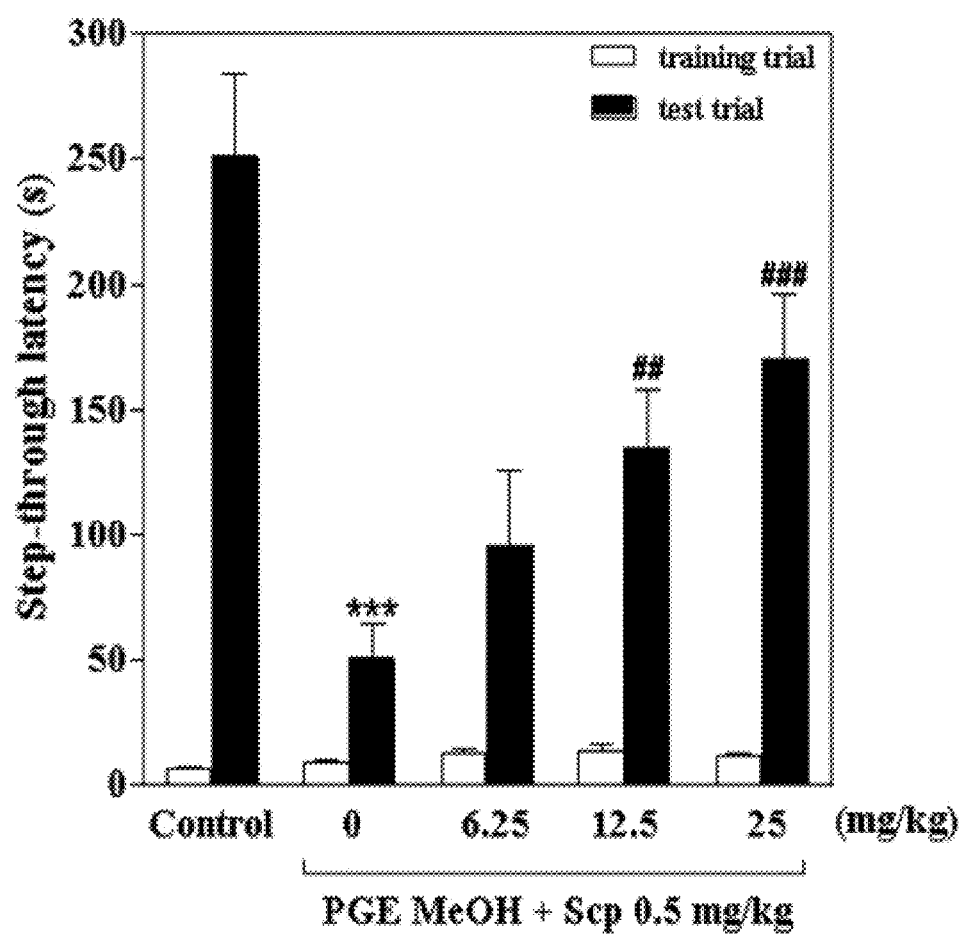
FIGS. 11A to 11D are diagrams showing effects of the *Portulaca grandiflora* Hook. extract or the fraction thereof on improvement of memory and the ability to learn using a passive avoidance test in a scopolamine-induced memory deficit model.
Figure 11B:
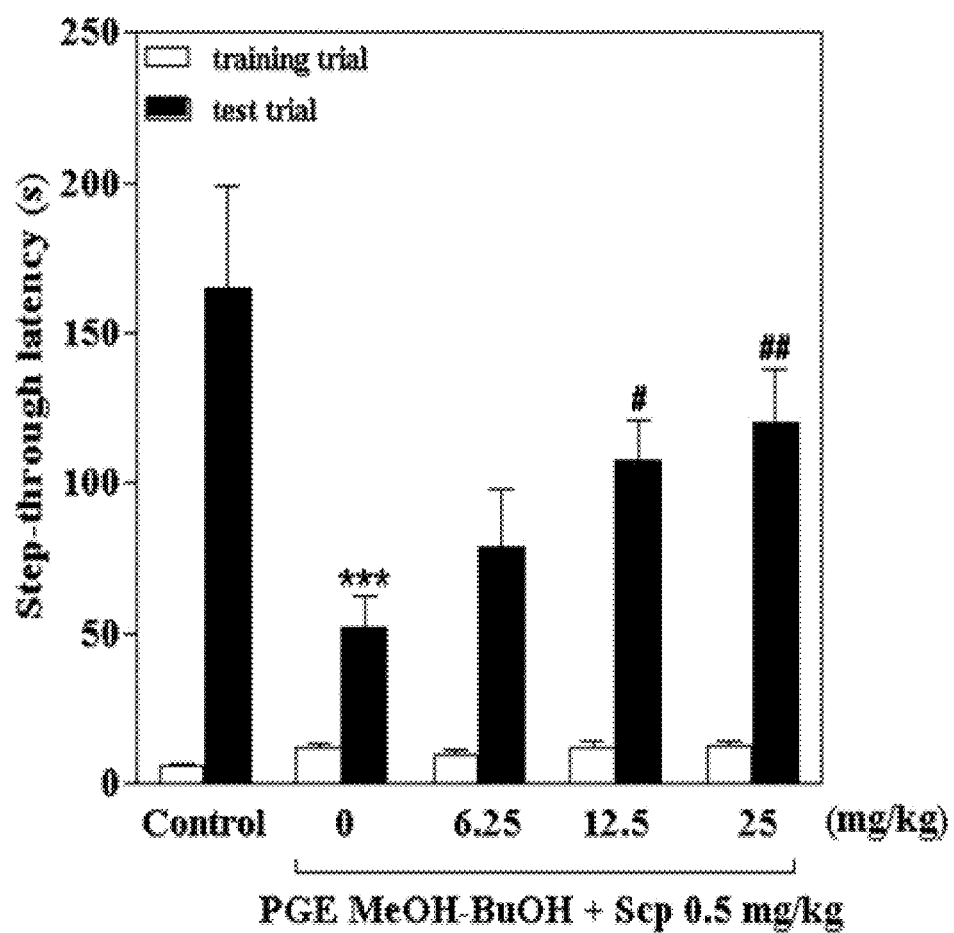
Figure 11C:
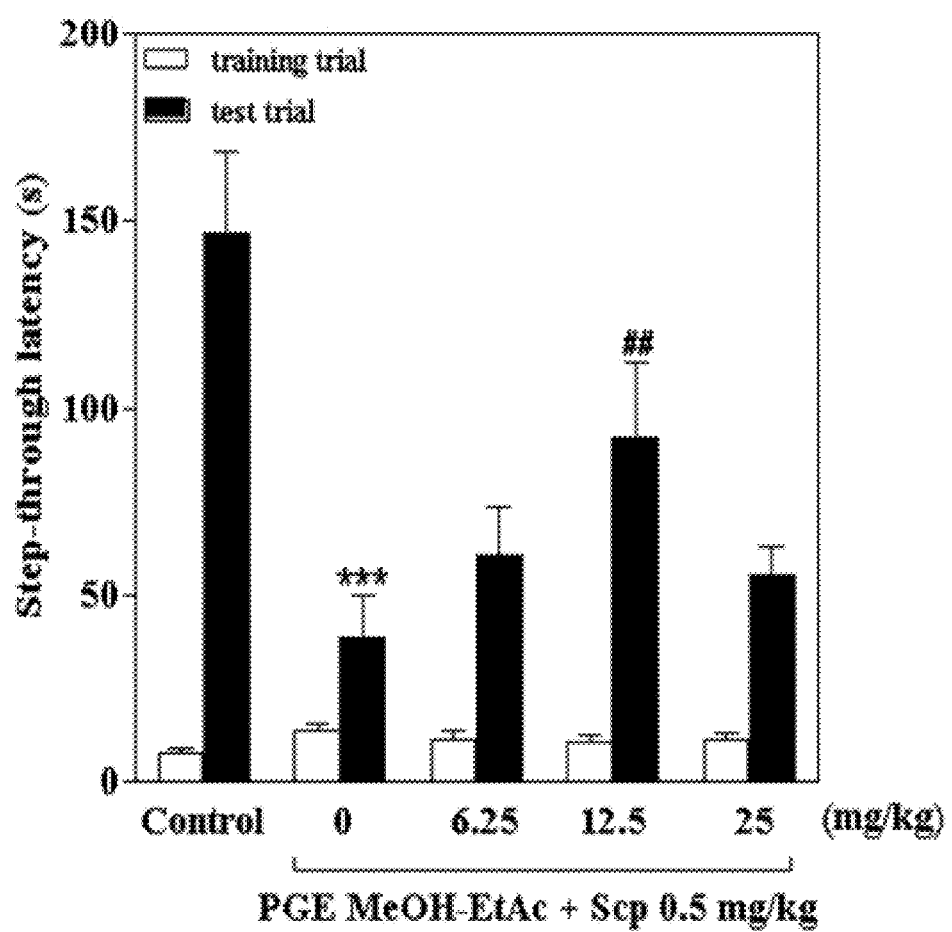
Figure 11D:
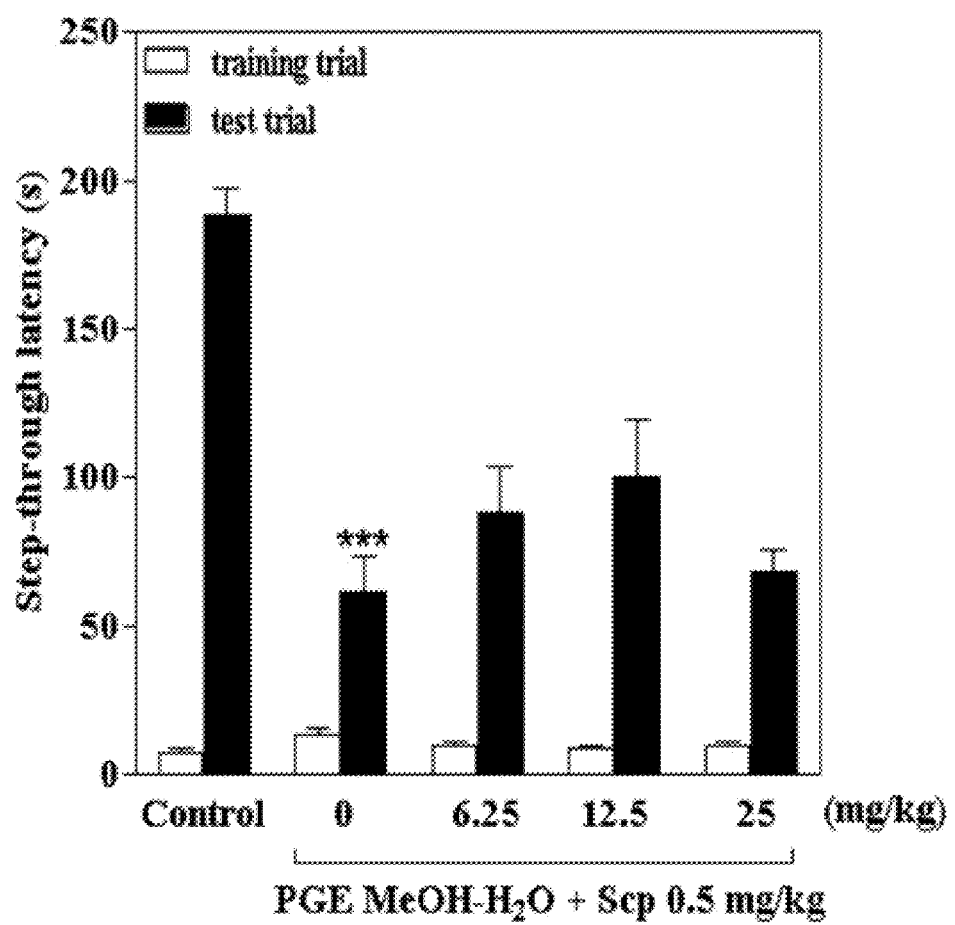

It was confirmed that the level of expression of the BACE1 protein and mRNA was also inhibited by the treated *Portulaca grandiflora* Hook. extract in a dose-dependent manner (FIGS. 7A and 7B).

Experimental Example 4: Effect of *Portulaca Grandiflora* Hook. Extract or Fractions Thereof on Increase in Working Memory Experimental Example 4-1: Confirmation of Effect of *Portulaca Grandiflora* Hook. Extract or Fractions Thereof on Increase in Working Memory Using Y-Maze Test Mice were divided into four groups, each group consisting of 14 mice. The first group was a group (control) to which distilled water including 10% Tween 20 was administered, and the second to fourth groups were groups (experimental groups) to which the *Portulaca grandiflora* Hook. extract or the butanol-, ethyl acetate-, and water-soluble fractions thereof were administered at a dose of 6.25, 12.5 and 25 mg/kg, respectively.

Each of the *Portulaca grandiflora* Hook. extract or fractions thereof was dissolved in distilled water including 10% Tween 20, and orally administered to mice at a dose of 6.25, 12.5 and 25 mg/kg. After an hour, the mice were placed in a Y-maze, and determined whether the mice freely entered each of A, B and C arms. In this case, one point was given when the mice entered a new arm, and the crossover behavior (%) was calculated according to the following Mathematical Equation 2.

$$\text{Crossover Behavior}(\%) = \frac{\text{Number of Times Mice Enter Three Arms}}{\text{Total Number of Times Mice Enter Each Arm} - 2} \times 100 \quad \text{[Mathematical Equation 2]}$$

As a result, it was confirmed that the crossover behavior (%) was increased by the *Portulaca grandiflora* Hook. extract or fraction thereof in a concentration-dependent manner in the mice of the second to fourth groups (experimental groups) to which the *Portulaca grandiflora* Hook. extract or fraction thereof was administered, compared to that of the mice of the first group (control) to which the *Portulaca grandiflora* Hook. extract or fraction thereof was not administered.

These results showed that the *Portulaca grandiflora* Hook. extract or fraction thereof had an effect of increasing the working memory in a Y-maze test. From the experimental results, it was confirmed that the *Portulaca grandiflora* Hook. methanol crude extract and fraction thereof remarkably increased the working memory of each mouse (FIGS. 8A to 8D).

Experimental Example 4-2: Confirmation of Effect of *Portulaca Grandiflora* Hook. Extract or Fractions Thereof on Improvement of Working Memory Using Y-Maze Test in Scopolamine-Induced Memory Deficit Model Mice were divided into five groups, each group consisting of 14 mice. The first group was a group (control) to which distilled water including 10% Tween 20 was administered, the second group was a group (positive control) to which scopolamine and distilled water including 10% Tween 20 were administered, and the third to fifth groups were groups (experimental groups) to which the *Portulaca grandiflora* Hook. extract or the butanol-, ethyl acetate- and water-soluble fractions thereof were administered.

Each of the *Portulaca grandiflora* Hook. extract or fractions thereof was dissolved in distilled water including 10% Tween 20, and orally administered to mice at a dose of 6.25, 12.5 and 25 mg/kg. After 30 minutes, 0.5 mg/kg of scopolamine was subcutaneously injected to the mice.

After an hour, the mice were placed in a Y-maze, and determined whether the mice freely entered each of A, B and C arms. In this case, one point was given when the mice entered a new arm, and the crossover behavior (%) was calculated according to the following Mathematical Equation 2.

$$\text{Crossover Behavior}(\%) = \frac{\text{Number of Times Mice Enter Three Arms}}{\text{Total Number of Times Mice Enter Each Arm} - 2} \times 100 \quad \text{[Mathematical Equation 2]}$$

As a result, it was confirmed that the crossover behavior (%) was reduced in the mice of the second group (positive control) to which scopolamine was administered, compared to that of the mice of the first group (control) to which scopolamine was not administered, indicating that the forgetfulness was induced.

Meanwhile, it was confirmed that the crossover behavior (%) was increased in the mice of the third to fifth groups (experimental groups) to which the *Portulaca grandiflora* Hook. extract or fractions thereof were administered. Based on the experimental results, it was confirmed that the *Portulaca grandiflora* Hook. methanol extract or fraction thereof effectively prevented the memory impairment (FIG. 9A to FIG. 9D).

Experimental Example 4-3: Confirmation of Effect of *Portulaca Grandiflora* Hook. Extract on Improvement of Working Memory Using Y-Maze Test in $A\beta_{25-35}$-Induced Dementia Model Mice were divided into five groups, each group consisting of 11 to 12 mice. The first group was a group (control) to which distilled water including 10% Tween 20 was administered, the second group was a group (positive control) to which $A\beta_{25-35}$ and distilled water including 10% Tween 20 were administered, and the third to fifth groups were groups (experimental groups) to which the *Portulaca grandiflora* Hook. extract was administered at different concentrations.

The *Portulaca grandiflora* Hook. extract was dissolved in distilled water including 10% Tween 20, and orally administered to the mice at a dose of 6.25, 12.5 and 25 mg/kg. After an hour, 6 nmol of $A\beta_{25-35}$ was injected to the left ventricles using a stereotaxic apparatus. The *Portulaca grandiflora* Hook. extract was administered to the mice of each of the groups at a dose of 6.25, 12.5 and 25 mg/kg for 5 days together with the distilled water including 10% Tween 20.

On the day 5, the mice were placed in a Y-maze after an hour of administration of the *Portulaca grandiflora* Hook. extract, and determined whether the mice freely entered each of A, B and C arms. In this case, one point was given when the mice entered a new arm, and the crossover behavior (%) was calculated according to the following Mathematical Equation 2.

$$\text{Crossover Behavior}(\%) = \frac{\text{Number of Times Mice Enter Three Arms}}{\text{Total Number of Times Mice Enter Each Arm} - 2} \times 100 \qquad \text{[Mathematical Equation 2]}$$

As a result, it was confirmed that the crossover behavior (52%) was reduced in the mice of the second group (positive control) to which $A\beta_{25-35}$ was administered, compared to the crossover behavior (67%) of the mice of the first group (control) to which $A\beta_{25-35}$ was not administered, indicating that dementia was induced (p<0.01).

Meanwhile, it was confirmed that the group to which the *Portulaca grandiflora* Hook. methanol extract was administered at a dose of 6.25 mg/kg, the group to which the *Portulaca grandiflora* Hook. methanol extract was administered at a dose of 12.5 mg/kg, and the group to which the *Portulaca grandiflora* Hook. methanol extract was administered at a dose of 25 mg/kg had a crossover behavior of 58%, 67%, and 62%, respectively, the values of which were remarkably increased, compared to that of the mice of the $A\beta_{25-35}$-induced dementia model group (positive control).

Figure 12:
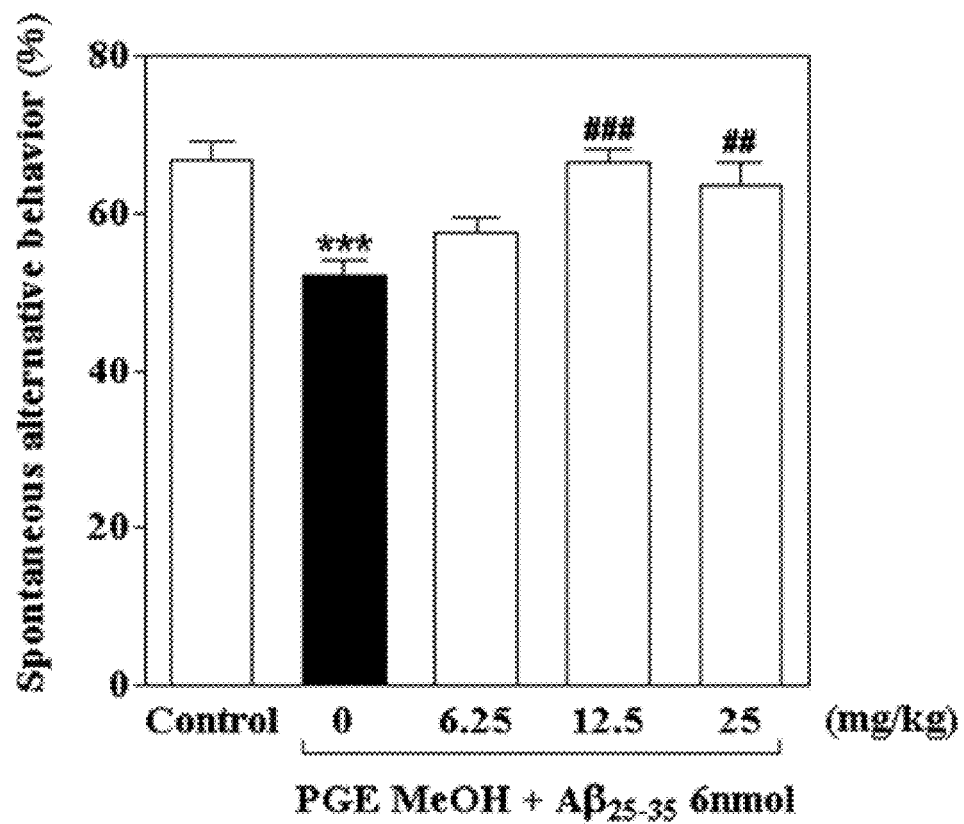
FIG. 12 is a diagram showing an effect of the *Portulaca grandiflora* Hook. extract or the fraction thereof on improvement of working memory using a Y-maze test in an $Aβ_{25-35}$-induced dementia model.

Based on the experimental results, it was confirmed that the *Portulaca grandiflora* Hook. extract effectively prevented the Alzheimer's memory impairment (FIG. 12).

Experimental Example 5: Effect of *Portulaca Grandiflora* Hook. Extract or Fractions Thereof on Increase in Memory and Ability to Learn Experimental Example 5-1: Confirmation of Effect of *Portulaca Grandiflora* Hook. Extract or Fractions Thereof on Increase in Memory and Ability to Learn Using Passive Avoidance Test Mice were divided into four groups, each group consisting of 11 to 12 mice. The first group was a group (control) to which distilled water including 10% Tween 20 was administered, and the second to fourth groups were groups (experimental groups) to which the *Portulaca grandiflora* Hook. extract or soluble fractions thereof (ethyl acetate, butanol, and water) were administered at a dose of 6.25, 12.5 and 25 mg/kg.

Each of the *Portulaca grandiflora* Hook. extract or soluble fractions thereof (ethyl acetate, butanol, and water) was dissolved in distilled water including 10% Tween 20, and orally administered to the mice at a dose of 6.25, 12.5 and 25 mg/kg. After an hour, the mice were placed in a step-through apparatus, and trained by applying an electric shock of 0.25 mA for 3 seconds when the mice entered a dark case. After 24 hours, a residence time from a time in which the mice were placed in a light case to a time in which the mice were returned back to the dark case was measured, and used as an indicator of memory and the ability to learn. In this case, a cut-off time of a mouse was set to 300 seconds, and then compared to that of the control.

As a result, it was confirmed that the residence time increased in the mice of the second to fourth groups (experimental groups) to which the *Portulaca grandiflora* Hook. extract or fractions thereof were administered, compared to that of the mice of the first group (control) to which the *Portulaca grandiflora* Hook. extract or fractions thereof were not administered.

From the experimental results, it was confirmed that the *Portulaca grandiflora* Hook. methanol crude extract and fraction thereof remarkably increased memory and the ability to learn (FIGS. 10A to 10D).

Experimental Example 5-2: Confirmation of Effect of *Portulaca Grandiflora* Hook. Extract or Fractions Thereof on Improvement of Memory and Ability to Learn Using Passive Avoidance Test in Scopolamine-Induced Memory Deficit Model Mice were divided into five groups, each group consisting of 14 mice. The first group was a group (control) to which distilled water including 10% Tween 20 was administered, the second group was a group (positive control) to which scopolamine and distilled water including 10% Tween 20 were administered, and the third to fifth groups were groups (experimental groups) to which the *Portulaca grandiflora* Hook. extract or soluble fractions thereof (ethyl acetate, butanol, and water) were administered.

Each of the *Portulaca grandiflora* Hook. extract or fractions thereof was dissolved in distilled water including 10% Tween 20, and orally administered to the mice at a dose of 6.25, 12.5 and 25 mg/kg. After 30 minutes, 0.5 mg/kg of scopolamine subcutaneously injected to the mice.

After 30 minutes, the mice were placed in a step-through apparatus, and trained by applying an electric shock of 0.25 mA for 3 seconds when the mice entered a dark case. After 24 hours, a residence time from a time in which the mice were placed in a light case to a time in which the mice were returned back to the dark case was measured, and used as an indicator of memory and the ability to learn for scopolamine-induced forgetfulness. In this case, a cut-off time of a mouse was set to 300 seconds, and then compared to that of the control.

As a result, it was confirmed that the residence time was shortened in the mice of the second group (positive control) to which the scopolamine was administered, compared to that of the mice of the first group (control) to which the scopolamine the was not administered, indicating that the forgetfulness was induced.

Meanwhile, it was confirmed that the residence time was increased in the mice of the third group to fifth groups (experimental groups) to which the *Portulaca grandiflora* Hook. extract or the ethyl acetate-, butanol-, and water-soluble fractions thereof were administered. Based on the experimental results, it was confirmed that the *Portulaca grandiflora* Hook. methanol extract or fraction thereof effectively prevented the memory impairment (FIGS. 11A to 11D).

Experimental Example 5-3: Confirmation of Effect of *Portulaca Grandiflora* Hook. Extract on Improvement of Memory and Ability to Learn Using Passive Avoidance Test in $A\beta_{325-35}$-Induced Dementia Model Mice were divided into five groups, each group consisting of 11 to 12 mice. The first group was a group (control) to which distilled water including 10% Tween 20 was administered, the second group was a group (positive control) to which $A\beta_{25-35}$ and distilled water including 10% Tween 20 were administered, and the third to fifth groups were groups (experimental groups) to which the *Portulaca grandiflora* Hook. methanol extract was administered at different concentrations.

The *Portulaca grandiflora* Hook. extract was dissolved in distilled water including 10% Tween 20, and orally administered to the mice at a dose of 6.25, 12.5 and 25 mg/kg. After an hour, 6 nmol of $A\beta_{25-35}$ was injected to the left ventricles using a stereotaxic apparatus. The *Portulaca grandiflora* Hook. extract was administered to the mice of each of the groups at a dose of 6.25, 12.5 and 25 mg/kg for 5 days together with the distilled water including 10% Tween 20.

After an hour, the mice were placed in a step-through apparatus, and trained by applying an electric shock of 0.3 mA for 3 seconds when the mice entered a dark case. After 24 hours, a residence time from a time in which the mice were placed in a light case to a time in which the mice were returned back to the dark case was measured, and used as an indicator of memory and the ability to learn for $A\beta_{25-35}$-induced dementia. In this case, a cut-off time of a mouse was set to 300 seconds, and then compared to that of the control.

As a result, it was confirmed that the residence time (73 seconds) was shortened in the mice of the second group (positive control) to which the s $A\beta_{25-35}$ was administered, compared to the residence time (218 seconds) of the mice of the first group (control) to which the $A\beta_{25-35}$ was not administered, indicating that the forgetfulness was significantly induced (p<0.001).

Meanwhile, it was confirmed that the group to which the *Portulaca grandiflora* Hook. methanol extract was administered at a dose of 6.25 mg/kg, the group to which the *Portulaca grandiflora* Hook. methanol extract was administered at a dose of 12.5 mg/kg, and the group to which the *Portulaca grandiflora* Hook. methanol extract was administered at a dose of 25 mg/kg had a residence time of 97 seconds, 163 seconds, and 153 seconds, respectively, the values of which were remarkably increased, compared to that of the mice of the $A\beta_{25-35}$-induced dementia model group (positive control).

Figure 13:
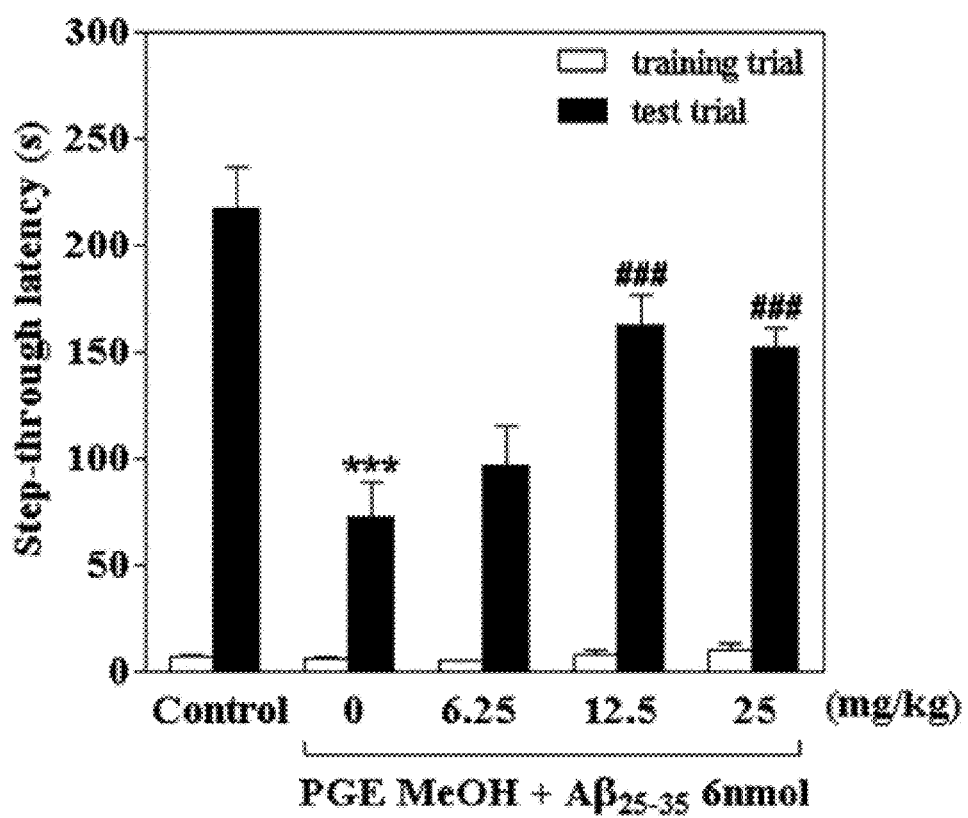
FIG. 13 is a diagram showing an effect of the *Portulaca grandiflora* Hook. extract or the fraction thereof on improvement of memory and the ability to learn using a passive avoidance test in an $Aβ_{25-35}$-induced dementia model.

Based on the experimental results, it was again confirmed that the *Portulaca grandiflora* Hook. extract was effective in effectively preventing the Alzheimer's memory impairment (FIG. 13).

The invention claimed is:

1. A method of preventing or treating neuroinflammation, comprising administering to a subject in need thereof a composition containing an effective amount of an aqueous and/or $C_1$ to $C_4$ lower alcohol extract of *Portulaca grandiflora* Hook. as an active ingredient,
wherein the extract is obtained by extracting ground parts of a whole plant of *Portulaca grandiflora* Hook., and
wherein the extract inhibits generation of nitrogen oxide (NO), production of prostaglandin E2 ($PGE_2$), and/or expression of proteins and mRNA of genes selected from the group consisting of iNOS, COX-2, β-CTF and BACE1.

2. The method of claim 1, wherein the $C_1$ to $C_4$ lower alcohol is methanol.

3. A method of preventing or treating neuroinflammation, comprising administering a food composition containing an aqueous and/or $C_1$ to $C_4$ lower alcohol extract of *Portulaca grandiflora* Hook. as an active ingredient to a subject in need thereof,
wherein the extract inhibits generation of nitrogen oxide (NO), production of prostaglandin E2 ($PGE_2$), and/or expression of proteins and mRNA of genes selected from the group consisting of iNOS, COX-2, β-CTF and BACE1.

4. A method of preventing or treating neuroinflammation, comprising
administering to a subject in need thereof a composition containing an effective amount of a fraction of an aqueous and/or $C_1$-$C_4$ lower alcoholic extract of *Portulaca grandiflora* Hook. as an active ingredient,
wherein the extract is obtained by extracting ground parts of a whole plant of *Portulaca grandiflora* Hook.,
wherein the fraction is obtained by fractionating the aqueous and/or $C_1$-$C_4$ lower alcoholic extract with: (a) ethyl acetate; (b) ethyl acetate and then butanol; or (c) ethyl acetate, butanol, and then water, and
wherein the fraction inhibits generation of nitrogen oxide (NO), production of prostaglandin E2 ($PGE_2$), and/or expression of proteins and mRNA of genes selected from the group consisting of iNOS, COX-2, β-CTF, and BACE1.

* * * * *

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: iNOS forward primer

<400> SEQUENCE: 1
cccttccgaa gtttctggca gcagc                                              25

<210> SEQ ID NO 2
<211> LENGTH: 25
<212> TYPE: DNA
<213> ORGANISM: Artificial Sequence
<220> FEATURE:
<223> OTHER INFORMATION: iNOS reverse primer

<400> SEQUENCE: 2
ggctgtcaga gcctcgtggc tttgg                                              25

<210> SEQ ID NO 3
<211> LENGTH: 20
<212> TYPE: DNA
<213> ORGANISM: Artificial Sequence
<220> FEATURE:
<223> OTHER INFORMATION: COX-2 forward primer

<400> SEQUENCE: 3
ttgaagacca ggagtacagc                                                    20

```
<210> SEQ ID NO 4
<211> LENGTH: 20
<212> TYPE: DNA
<213> ORGANISM: Artificial Sequence
<220> FEATURE:
<223> OTHER INFORMATION: COX-2 reverse primer

<400> SEQUENCE: 4
ggtacagttc catgacatcg                                                  20

<210> SEQ ID NO 5
<211> LENGTH: 20
<212> TYPE: DNA
<213> ORGANISM: Artificial Sequence
<220> FEATURE:
<223> OTHER INFORMATION: beta-actin forward primer

<400> SEQUENCE: 5
agccatgtac gtagccatcc                                                  20

<210> SEQ ID NO 6
<211> LENGTH: 20
<212> TYPE: DNA
<213> ORGANISM: Artificial Sequence
<220> FEATURE:
<223> OTHER INFORMATION: beta-actin reverse primer

<400> SEQUENCE: 6
gctgtggtgg tgaagctgta                                                  20

<210> SEQ ID NO 7
<211> LENGTH: 24
<212> TYPE: DNA
<213> ORGANISM: Artificial Sequence
<220> FEATURE:
<223> OTHER INFORMATION: BACE1 forward primer

<400> SEQUENCE: 7
cattggaggt atcgaccact cgct                                             24

<210> SEQ ID NO 8
<211> LENGTH: 24
<212> TYPE: DNA
<213> ORGANISM: Artificial Sequence
<220> FEATURE:
<223> OTHER INFORMATION: BACE1 reverse primer

<400> SEQUENCE: 8
ccacagtctt ccatgtccaa ggtg                                             24
```